United States Patent
Hoon et al.

(10) Patent No.: US 7,943,319 B2
(45) Date of Patent: May 17, 2011

(54) UTILITY OF RET MUTANT IN DIAGNOSIS AND TREATMENT OF MELANOMA

(75) Inventors: Dave S. B. Hoon, Los Angeles, CA (US); Norihiko Narita, Fukui (JP); Atsushi Tanemura, Osaka (JP)

(73) Assignee: John Wayne Cancer Institute, Santa Monica, CA (US)

( * ) Notice: Subject to any disclaimer, the term of this patent is extended or adjusted under 35 U.S.C. 154(b) by 190 days.

(21) Appl. No.: 12/267,541

(22) Filed: Nov. 7, 2008

(65) Prior Publication Data

US 2009/0208952 A1    Aug. 20, 2009

Related U.S. Application Data

(60) Provisional application No. 61/002,606, filed on Nov. 9, 2007.

(51) Int. Cl.
*C12Q 1/68* (2006.01)
*C12P 19/34* (2006.01)
*C07H 21/02* (2006.01)
*C07H 21/04* (2006.01)
*G01N 33/53* (2006.01)
*G01N 33/574* (2006.01)
*C07K 14/435* (2006.01)

(52) U.S. Cl. ............. 435/6; 435/4; 435/7.1; 435/91.2; 536/23.5; 530/350

(58) Field of Classification Search .................. None
See application file for complete search history.

(56) References Cited

OTHER PUBLICATIONS

GeneCard for the RET gene available via url: <genecards.org/cgi-bin/carddisp.pl?gene=ret>, printed on Oct. 6, 2010.*
GeneCard for the BRAF gene available via url: <genecards.org/cgi-bin/carddisp.pl?gene=BRAF>, printed on Oct. 6, 2010.*
Hirschhorn et al. Genetics in Medicine. vol. 4, No. 2, pp. 45-61, Mar. 2002.*
Lucentini et al. The Scientist (2004) vol. 18, p. 20.*
Wacholder et al. J. Natl. Cancer Institute (2004) 96(6):434-442.*
Halushka et al. Nature. Jul. 1999. 22: 239-247.*
van der Harst. Int J Cancer. 1998. 79: 537-540.*
Chevalier et al. International Journal of Andrology. 2009. no. doi: : 10.1111/j.1365-2605.*
Sawai et al. Cancer Research. 2005. 65(24): 11536-11544.*
Airaksinen MS and Saarma M. The GDNF family: signalling, biological functions and therapeutic value. Nat Rev Neurosci 2002;3:383-94.
Bounacer A, Du Villard JA, Wicker R, et al. Association of RET codon 691 polymorphism in radiation-induced human thyroid tumours with C-cell hyperplasia in peritumoural tissue. Br J Cancer 2002;86:1929-36.
Busam KJ. Cutaneous desmoplastic melanoma. Adv Anat Pathol 2005;12:92-102.
Busam KJ, Zhao H, Coit DG, et al. Distinction of desmoplastic melanoma from non-desmoplastic melanoma by gene expression profiling. J Invest Dermatol 2005;124:412-8.
Carlomagno F, Anaganti S, Guida T, et al. BAY 43-9006 inhibition of oncogenic RET mutants. J Natl Cancer Inst 2006;98:326-34.
Ceccherini I, Hofstra RM, Luo Y, et al. DNA polymorphisms and conditions for SSCP analysis of the 20 exons of the ret proto-oncogene. Oncogene 1994;9:3025-9.
Curtin JA, Busam K, Pinkel D, and Bastian BC. Somatic activation of KIT in distinct subtypes of melanoma. J Clin Oncol 2006;24:4340-6.
Davies H, Bignell GR, Cox C, et al. Mutations of the BRAF gene in human cancer. Nature 2002;417:949-54.
Davison JM, Rosenbaum E, Barrett TL, et al. Absence of V599E BRAF mutations in desmoplastic melanomas. Cancer 2005;103:788-92.
Dhomen N and Marais R. New insight into BRAF mutations in cancer. Curr Opin Genet Dev 2007;17:31-9.
Elisei R, Cosci B, Romei C, et al. RET exon 11 (G691S) polymorphism is significantly more frequent in sporadic medullary thyroid carcinoma than in the general population. J Clin Endocrinol Metab 2004;89:3579-84.
Fujiwara Y, Chi DD, Wang H, et al. Plasma DNA microsatellites as tumor-specific markers and indicators of tumor progression in melanoma patients. Cancer Res 1999;59:1567-71.
Goto Y, Matsuzaki Y, Kurihara S, et al. A new melanoma antigen fatty acid-binding protein 7, involved in proliferation and invasion, is a potential target for immunotherapy and molecular target therapy. Cancer Res 2006;66:4443-9.
Govindarajan B, Sligh JE, Vincent BJ, et al. Overexpression of Akt converts radial growth melanoma to vertical growth melanoma. J Clin Invest 2007;117:719-29.
Gumireddy K, Sun F, Klein-Szanto AJ, et al. In vivo selection for metastasis promoting genes in the mouse. Proc Natl Acad Sci U S A 2007;104:6696-701.
Hoon DS, Kuo CT, Wascher RA, Fournier P, Wang HJ, and O'Day SJ. Molecular detection of metastatic melanoma cells in cerebrospinal fluid in melanoma patients. J Invest Dermatol 2001;117:375-8.
Iwamoto T, Taniguchi M, Asai N, Ohkusu K, Nakashima I, and Takahashi M. cDNA cloning of mouse ret proto-oncogene and its sequence similarity to the cadherin superfamily. Oncogene 1993;8:1087-91.
Jaroszewski DE, Pockaj BA, DiCaudo DJ, and Bite U. The clinical behavior of desmoplastic melanoma. Am J Surg 2001;182:590-5.
Kato et al., "Transgenic mouse model for skin malignant melanoma," Oncogene 1998, vol. 17, pp. 1885-1888.
Kodama Y, Asai N, Kawai K, et al. The RET proto-oncogene: a molecular therapeutic target in thyroid cancer. Cancer Sci 2005;96:143-8.
Kumar et al., "BRAF mutations in metastatic melanoma: a possible association with clinical outcome," Clinical Cancer Research, Aug. 15, 2003, vol. 9, pp. 3362-3368.
Kondo T, Ezzat S, and Asa SL. Pathogenetic mechanisms in thyroid follicular-cell neoplasia. Nat Rev Cancer 2006;6:292-306.
Koyanagi K, O'Day SJ, Gonzalez R, et al. Serial monitoring of circulating melanoma cells during neoadjuvant biochemotherapy for stage III melanoma: outcome prediction in a multicenter trial. J Clin Oncol 2005;23:8057-64.
Lin LF, Doherty DH, Lile JD, Bektesh S, and Collins F. GDNF: a glial cell line-derived neurotrophic factor for midbrain dopaminergic neurons. Science 1993;260:1130-2.

(Continued)

*Primary Examiner* — Carla Myers
(74) *Attorney, Agent, or Firm* — Perkins Coie LLP

(57) ABSTRACT

The invention relates to a method of detecting a RET mutant in a melanoma cell. Also disclosed is a method of modulating the activity of a RET mutant in a melanoma cell with an agent that interferes with the activity of the RET mutant.

6 Claims, 16 Drawing Sheets

OTHER PUBLICATIONS

Liu et al., "Sorafenib blocks the RAF/MEK/ERK pathway, inhibits tumor angiogenesis, and induces tumor cell apoptosis in hepatocellular carcinoma model PLC/PRF/5," Cancer Research, 2006, vol. 66, pp. 11851-11858.

Livestro DP, Muzikansky A, Kaine EM, et al. Biology of desmoplastic melanoma: a case-control comparison with other melanomas. J Clin Oncol 2005;23:6739-46.

Melillo RM, Castellone MD, Guarino V, et al. The RET/PTC-RAS-BRAF linear signaling cascade mediates the motile and mitogenic phenotype of thyroid cancer cells. J Clin Invest 2005;115:1068-81.

Mologni L, Sala E, Cazzaniga S, et al. Inhibition of RET tyrosine kinase by SU5416. J Mol Endocrinol 2006;37:199-212.

Plaza-Menacho I, Mologni L, Sala E, et al. Sorafenib functions to potently suppress RET tyrosine kinase activity by direct enzymatic inhibition and promoting RET lysosomal degradation independent of proteasomal targeting. J Biol Chem 2007;282:29230-40.

Quinn MJ, Crotty KA, Thompson JF, Coates AS, O'Brien CJ, and McCarthy WH. Desmoplastic and desmoplastic neurotropic melanoma: experience with 280 patients. Cancer 1998;83:1128-35.

Runeberg-Roos P and Saarma M. Neurotrophic factor receptor RET: structure, cell biology, and inherited diseases. Ann Med 2007:1-9.

Satyamoorthy K, Li G, Gerrero MR, et al. Constitutive mitogen-activated protein kinase activation in melanoma is mediated by both BRAF mutations and autocrine growth factor stimulation. Cancer Res 2003;63:756-9.

Sawai H, Okada Y, Kazanjian K, et al. The G691S RET polymorphism increases glial cell line-derived neurotrophic factor-induced pancreatic cancer cell invasion by amplifying mitogen-activated protein kinase signaling. Cancer Res 2005;65:11536-44.

Selek U, Chang EL, Hassenbusch SJ, 3rd, et al. Stereotactic radiosurgical treatment in 103 patients for 153 cerebral melanoma metastases. Int J Radiat Oncol Biol Phys 2004;59:1097-106.

Shinozaki M, Fujimoto A, Morton DL, and Hoon DS. Incidence of BRAF oncogene mutation and clinical relevance for primary cutaneous melanomas. Clin Cancer Res 2004;10:1753-7.

Shinozaki M, O'Day SJ, Kitago M, et al. Utility of circulating B-RAF DNA mutation in serum for monitoring melanoma patients receiving biochemotherapy. Clin Cancer Res 2007;13:2068-74.

Stephens LA, Powell NG, Grubb J, et al. Investigation of loss of heterozygosity and SNP frequencies in the RET gene in papillary thyroid carcinoma. Thyroid 2005;15:100-4.

Sumimoto H, Miyagishi M, Miyoshi H, et al. Inhibition of growth and invasive ability of melanoma by inactivation of mutated BRAF with lentivirus-mediated RNA interference. Oncogene 2004;23:6031-9.

Takahashi M, Buma Y, Iwamoto T, Inaguma Y, Ikeda H, and Hiai H. Cloning and expression of the ret proto-oncogene encoding a tyrosine kinase with two potential transmembrane domains. Oncogene 1988;3:571-8.

Takahashi M. The GDNF/RET signaling pathway and human diseases. Cytokine Growth Factor Rev 2001;12:361-73.

Takahashi M, Buma Y, and Hiai H. Isolation of ret proto-oncogene cDNA with an amino-terminal signal sequence. Oncogene 1989;4:805-6.

Umetani N, Mori T, Koyanagi K, et al. Aberrant hypermethylation of ID4 gene promoter region increases risk of lymph node metastasis in T1 breast cancer. Oncogene 2005;24:4721-7.

United States Patent and Trademark Office, International Search Report and Written Opinion for PCT/US08/82914, mailed Feb. 4, 2009.

Weber F and Eng C. Update on the molecular diagnosis of endocrine tumors: toward omics-based personalized healthcare? J Clin Endocrinol Metab 2008;93:1097-104.

Zbuk KM and Eng C. Cancer phenomics: RET and PTEN as illustrative models. Nat Rev Cancer 2007;7:35-45.

\* cited by examiner

UTILITY OF RET MUTANT IN DIAGNOSIS AND TREATMENT OF MELANOMA

RELATED APPLICATION

This application claims priority to U.S. Provisional Application Ser. No. 61/002,606, filed on Nov. 9, 2007, the content of which is incorporated herein by reference in its entirety.

FUNDING

This invention was made with support in part by NIH NCI Project II P0 CA029605 and CA012582 grants. Therefore, the U.S. government has certain rights.

FIELD OF THE INVENTION

The present invention relates in general to diagnosis and treatment of cancer. More specifically, the invention provides a method of using a RET mutant such as RET G691S (RETmt) as a biomarker for detection of melanoma and a target for treatment of the disease.

BACKGROUND OF THE INVENTION

Melanoma is of neuroectodermal origin and has a high propensity to invade and metastasize, particularly to neural-origin tissue, such as the central nervous system and brain, which often contributes to its poor prognosis (1). Desmoplastic melanoma (DM) is a subtype of cutaneous melanoma, with distinct clinico-pathologic characteristics that distinguish it from other cutaneous melanomas (2). DMs often arise in sun-exposed areas, especially the head and neck region, and have a greater propensity for invasion of nerves and aggressive local growth (3, 4). Reports have shown more frequent local recurrence of DMs compared to non-desmoplastic cutaneous melanomas (5). A distinction between DMs and non-DMs has been reported. However, no reported studies have analyzed mechanisms of neurotropism or local aggressiveness of DMs or non-DMs.

RET (REarranged during Transfection) is a proto-oncogene that encodes a receptor tyrosine kinase (RTK) (6-9). RET contains four cadherin-related motifs and a cysteine-rich region in the extracellular domain (8, 10). GDNF, a major ligand of RET, is a growth factor that facilitates the survival of dopaminergic neurons of the midbrain (11, 12). This neurotrophic factor binds to the extracellular domain of RET through the formation of a complex with glycosyl-phosphatidylinositol-anchored coreceptor (GFRα1-3), a member of the GDNF receptor family that can bind to GDNF and RET (10). Expression of GFRα3 is higher in DMs than non-DMs (13), but has not been linked to neurotropism of DMs.

Activation of RET induces signaling through the RAS-BRAF-ERK, phosphatidylinositol 3-kinase (PI3K)-Akt, and p38 mitogen-activated protein kinase (MAPK) pathways that activate various functions in cells (10). Activation of both the RET-RAS-BRAF-ERK and RET-PI3K-Akt pathways has been implicated in cell proliferation or survival, whereas the RET-PI3K pathway has been related more to cell motility (FIG. 1) (10, 14). All oncogenic mutations of RET gene, which are reported to be in cysteine-rich region or tyrosine kinase domain (intracellular domain), are ligand-independently active and reportedly responsible for development of multiple endocrine neoplasia 2A and 2B, familial medullary thyroid carcinoma, and papillary thyroid carcinoma (15-17). G691S RET mutation (RETmt) is a polymorphic nucleotide alteration in exon 11 of the juxtamembrane region of RET and enhances the response of RET against GDNF in pancreatic cancer (18).

BRAF mutations are well-documented, and are frequent in non-DMs (19). The most frequent BRAF mutation is a polymorphism in exon 15, V600E (19, 20). BRAF belongs to the RAF family of serine-threonine kinases and is a component of the RET-RAS-BRAF-MAPK kinase (MEK)-ERK signaling pathway (21). This signaling pathway is a membrane-to-nucleus signaling system controlling cell proliferation and other functions in mammalian cells (22). Although V600E BRAF mutation (BRAFmt) is suggested to cause abnormal proliferation of melanoma cells (23), the role of RETmt alone and with BRAFmt in cutaneous melanoma is unknown.

SUMMARY OF THE INVENTION

The present invention is based, at least in part, upon the unexpected discovery of RETmt in melanoma cells.

Accordingly, in one aspect, the invention features a method of detecting a RET (REarranged during Transfection) mutant in a melanoma cell. The method comprises providing a melanoma cell and detecting the RET mutant in the cell. The melanoma cell may be a cultured cell or a cell isolated from a subject suffering from melanoma. The method may further comprise detecting a BRAF (V-raf murine sarcoma viral oncogene homolog B1) mutant in the cell.

In another aspect, the invention features a method of modulating the activity of a RET mutant in a melanoma cell. The method comprises providing a melanoma cell containing a RET mutant and contacting the cell with an agent that interferes with the activity of the RET mutant. In some embodiments, the melanoma cell further contains a BRAF mutant.

The agent may interfere with the interaction between the RET mutant and GDNF (glial cell line-derived neurotrophic factor). In some embodiments, the agent interferes with the signal transduction through a pathway comprising the RET mutant and RAS (rat sarcoma). For example, the agent may interfere with cell proliferation, migration, or invasion, or the phosphorylation of ERK1/2 (Extracellular Signal-Regulated Kinase 1/2). In some embodiments, the agent interferes with the signal transduction through a pathway comprising the RET mutant and PI3K (phosphatidylinositol-3-Kinase). For example, the agent may interfere with cell proliferation, migration, or invasion, or the phosphorylation of Akt (protein kinase B). In some embodiments, the agent is a RTK (receptor tyrosine kinase) inhibitor such as sorafenib or semaxanib. In some embodiments, the agent is an antibody, peptide, or siRNA against the RET mutant.

In some embodiments, the RET mutant is RETmt (RET G691S). In some embodiments, the BRAF mutant is BRAFmt (B3RAF V600E). The melanoma may be DM (desmoplastic melanoma), non-DM, metastatic, or primary.

Unless otherwise defined, all technical and scientific terms used herein have the same meaning as commonly understood by one of ordinary skill in the art to which this invention pertains. In case of conflict, the present document, including definitions, will control. The materials, methods, and examples disclosed herein are illustrative only and not intended to be limiting. Other features, objects, and advantages of the invention will be apparent from the description and the accompanying drawings, and from the claims.

DETAILED DESCRIPTION OF THE INVENTION

Figure 1:
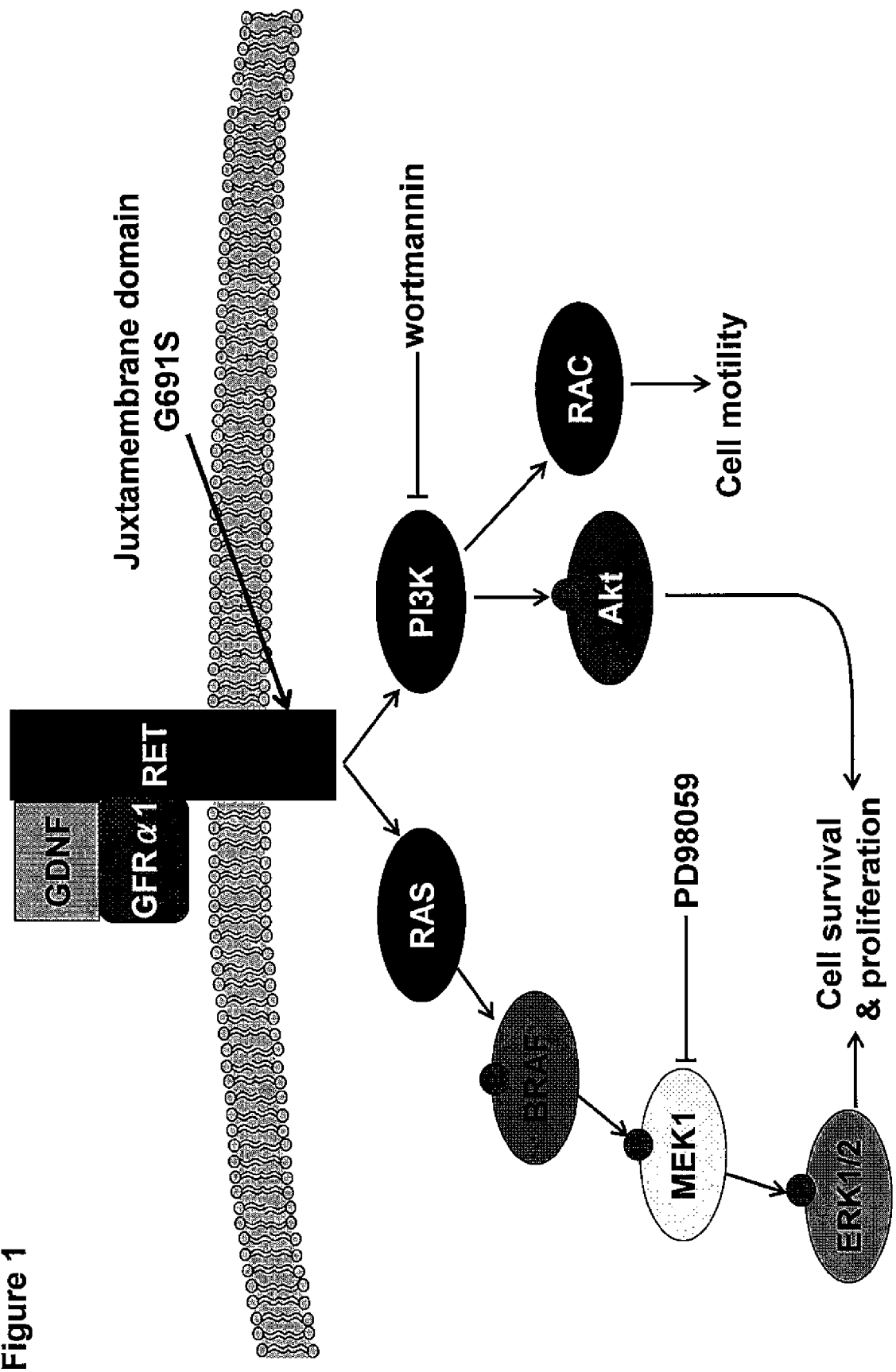
FIG. 1. Schematic diagram of signaling pathway of RET activation leading to cell proliferation and motility.

Cutaneous melanomas, particularly the desmoplastic subtype, have a strong propensity to invade neural-derived tissues. RET proto-oncogene encodes a receptor tyrosine kinase whose ligand is glial cell line-derived neurotrophic factor (GDNF). The frequency of RET mutation at G691S juxtamembrane region (RETmt) in cutaneous melanoma was determined. RETmt was functionally responsive to GDNF. RETmt was assessed in 71 non-desmoplastic cutaneous melanomas (non-DMs) and 70 desmoplastic melanomas (DMs). Established melanoma cell lines with RETmt, RET wild-type (RETwt), BRAF V600E mutation (BRAFmt) or BRAF wild-type (BRAFwt) were assessed for functional activity in vitro. RETmt frequency was significantly higher in DMs (61%) than in non-DMs (31%, $P<0.001$). BRAFmt was detected in only 11% of DMs. RETmt was demonstrated to be acquired in cutaneous melanomas. Its functional activity was investigated. GDNF stimulation significantly amplified cell proliferation, migration, and invasion in RETmt, but not in RETwt melanoma cells. GDNF stimulation of RETmt cell lines enhanced phosphorylation of extracellular signal-regulated kinase (ERK) and Akt of the RET-RAS-RAF-ERK and RET-phosphatidylinositol 3-kinase (PI3K)-Akt pathways, respectively. GDNF response of RETmt cells for signal transduction or functional cell studies was not affected by BRAFmt. The study demonstrates that RETmt in cutaneous melanoma frequently occurs, and responds to GDNF inducing events favorable for supporting tumor progression. Therefore, RETmt may serve as a therapeutic target for receptor tyrosine kinase inhibitors in melanomas.

Accordingly, the invention first provides a method of detecting a RET mutant in melanoma cells. In this method, the melanoma cells may be provided as a culture or isolated from a subject suffering from melanoma using any of the methods well known in the art. The melanoma may be DM, non-DM, metastatic, or primary.

As used herein, a "wild-type" refers to the typical form of a gene as it occurs in nature, the transcript of the gene, or the protein encoded by the gene; a "mutant" refers to a form of a gene arising or resulting from an instance of mutation, which is a structural change within the DNA of a gene resulting in the creation of a new gene different from the wild-type gene, the transcript of the mutated gene, or the protein encoded by the mutated gene.

The RET gene encodes a receptor tyrosine kinase. Mutations in the RET gene are known to be present at multiple sites. For example, RETmt (RET G691S) is a polymorphic nucleotide alteration (GGT→AGT) in exon 11 of the juxtamembrane region of RET.

As used herein, a "subject" refers to a human or animal, including all mammals such as primates (particularly higher primates), sheep, dog, rodents (e.g., mouse or rat), guinea pig, goat, pig, cat, rabbit, and cow. In a preferred embodiment, the subject is a human. In another embodiment, the subject is an experimental animal or animal suitable as a disease model.

The RET mutant gene, transcript, and protein may be detected in cultured cells or cells isolated from a subject using any of the methods described in the instant application or those well known in the art. For instance, a RET mutant may be detected by Southern blot, PCR, sequencing, a peptide nucleic acid-locked nucleic acid clamp method, Northern blot, RT-PCR, immunohistochemistry, Western blot, and the like.

The invention also provides a method of detecting a RET mutant such as RETmt in normal skin cells isolated from a subject suffering from melanoma. Normal skin cells can be isolated from a subject suffering from melanoma using any of the methods well known in the art. The RET mutant may be detected as described above.

The BRAF gene encodes a serine threonine kinase downstream for RAS in the MAP kinase pathway that transduces regulatory signals from RAS through MAPK. Mutations in the BRAF gene are known to be present at multiple sites, and clustering around exons 11 and 15 of the gene in the kinase domain is quite frequent. For example, the V600E (formerly V599E) amino acid missense mutation resulting from a 1796T→A transversion in exon 15 is the predominant mutation in melanoma.

A method of the invention may further include a step of detecting a BRAF mutant in the melanoma cells using the methods described above. The presence of both RET and BRAF mutants in the cells indicates that RTK targeting therapy may be more active towards the tumor cells.

In addition, the invention provides a method of modulating the activity of a RET mutant in melanoma cells in vivo and in vitro. The method involves the steps of providing melanoma cells containing a RET mutant and contacting the cells with an agent that interferes with the activity of the RET mutant. Melanoma cells containing a RET mutant can be identified as described above. As used herein, "the activity of a RET mutant" refers to any biological role a RET mutant plays, including but not limited to the replication or transcription of a RET mutant gene, the processing (e.g., splicing, editing, 5'-end capping, and 3'-polyadenylation), transport, and translation of a RET mutant transcript, and the function of a RET mutant protein (e.g., signal transduction through interacting with GDNF and GFRα1-3, the RAS-BRAF-MEK-ERK pathway, the PI3K-Akt pathway, and the PI3K-RAC pathway).

An agent may interfere with the activity of a RET mutant in many ways, for example, by interfering with the interaction between the RET mutant and GDNF, the signal transduction through a pathway comprising the RET mutant and RAS or PI3K, cell proliferation, migration, or invasion, or the phosphorylation of ERK1/2 or Akt. Such an agent may be, for example, a RTK inhibitor such as sorafenib or semaxanib, or an antibody, peptide, or siRNA against the RET mutant.

An agent that interferes with the activity of a RET mutant can be used for treating melanoma having the RET mutant by administering an effective amount of such an agent to a subject suffering from the melanoma.

A subject to be treated may be identified in the judgment of the subject or a health care professional, which can be subjective (e.g., opinion) or objective (e.g., reached by detecting the RET mutant in the melanoma as described above).

A "treatment" is defined as administration of a substance to a subject with the purpose to cure, alleviate, relieve, remedy, prevent, or ameliorate a disorder, symptoms of the disorder, a disease state secondary to the disorder, or predisposition toward the disorder.

An "effective amount" is an amount of a compound that is capable of producing a medically desirable result in a treated subject. The medically desirable result may be objective (i.e., measurable by some test or marker) or subjective (i.e., subject gives an indication of or feels an effect).

For treatment of cancer, a compound is preferably delivered directly to tumor cells, e.g., to a tumor or a tumor bed following surgical excision of the tumor, in order to treat any remaining tumor cells. For prevention of cancer invasion and metastases, the compound can be administered to, for example, a subject that has not yet developed detectable invasion and metastases but is found to have a RET mutant.

The compounds can be incorporated into pharmaceutical compositions. Such compositions typically include the compounds and pharmaceutically acceptable carriers. "Pharmaceutically acceptable carriers" include solvents, dispersion media, coatings, antibacterial and antifungal agents, isotonic and absorption delaying agents, and the like, compatible with pharmaceutical administration.

A pharmaceutical composition is formulated to be compatible with its intended route of administration. See, e.g., U.S. Pat. No. 6,756,196. Examples of routes of administration include parenteral, e.g., intravenous, intradermal, subcutaneous, oral (e.g., inhalation), transdermal (topical), transmucosal and rectal administration.

It is advantageous to formulate oral or parenteral compositions in dosage unit form for ease of administration and uniformity of dosage. "Dosage unit form," as used herein, refers to physically discrete units suited as unitary dosages for the subject to be treated, each unit containing a predetermined quantity of an active compound calculated to produce the desired therapeutic effect in association with the required pharmaceutical carrier.

The dosage required for treating a subject depends on the choice of the route of administration, the nature of the formulation, the nature of the subject's illness, the subject's size, weight, surface area, age, and sex, other drugs being administered, and the judgment of the attending physician. Suitable dosages are in the range of 0.01-100.0 mg/kg. Wide variations in the needed dosage are to be expected in view of the variety of compounds available and the different efficiencies of various routes of administration. For example, oral administration would be expected to require higher dosages than administration by intravenous injection. Variations in these dosage levels can be adjusted using standard empirical routines for optimization as is well understood in the art. Encapsulation of the compound in a suitable delivery vehicle (e.g., polymeric microparticles or implantable devices) may increase the efficiency of delivery, particularly for oral delivery.

When the melanoma cells also contain a BRAF mutant, a method of the invention may further involve contacting the cells with an agent that interferes with the activity of the BRAF mutant or administering an effective amount of such an agent to the subject suffering from the melanoma. Melanoma cells containing a BRAF mutant can be identified as described above. As used herein, "the activity of a BRAF mutant" refers to any biological role a BRAF mutant plays, including but not limited to the replication or transcription of a BRAF mutant gene, the processing (e.g., splicing, editing, 5'-end capping, and 3'-polyadenylation), transport, and translation of a BRAF mutant transcript, and the function of a BRAF mutant protein (e.g., signal transduction through the RAS-BRAF-MEK-ERK pathway).

The following example is intended to illustrate, but not to limit, the scope of the invention. While such example is typical of those that might be used, other procedures known to those skilled in the art may alternatively be utilized. Indeed, those of ordinary skill in the art can readily envision and produce further embodiments, based on the teachings herein, without undue experimentation.

EXAMPLE

Functional RET G691S Mutation in Cutaneous Malignant Melanoma

In this study, the frequency of RETmt in DMs and non-DMs was assessed. We found that RETmt is frequently present in cutaneous melanomas, and more frequent in desmoplastic melanomas invading neural tissues. RETmt was shown to be highly responsive to the ligand GDNF inducing various physiological activity. This is the first report describing the detection and functional activity of RETmt in cutaneous melanomas.

Materials and Methods
Cell Lines

All 11 melanoma cell lines (ME1, ME2, ME3, ME5, ME7, ME8, ME10, ME13, ME20, M16, and M20) used in the present study were established at the John Wayne Cancer Institute (JWCI) and cultured as described previously (24). All melanoma cell lines were used for quantitative real-time PCR analyses of RET, GFRα1, and GFRα3. Six cell lines (ME1, ME3, ME5, ME7, ME10, and M16) were selected for functional assays based on the presence of RETmt, RETwt, BRAFmt, and BRAFwt. MIAPaCa-2, PANC-1 (human pancreatic cancer), and MCF-7 (human breast cancer) were obtained from American Type Culture Collection (Rockville, Md.). Human normal melanocytes (HMC) and normal brain tissues (B336929, B37876) were purchased from Cascade Biologics, Inc. (Portland, Oreg.) and Cooperative Human Tissue Network (Philadelphia, Pa.), respectively.

Tissue Specimens

Formalin-fixed, paraffin-embedded blocks of resected tumor tissue were obtained for 71 patients with non-DM and 70 patients with DM. All patients had undergone surgical treatment of primary or metastatic melanoma at Saint John's Health Center (SJHC) or Sydney Melanoma Unit (SMU). Two different sources of tissues relative to countries were used to prevent bias of any regional influence. Use of human specimens in this study was approved by the institutional review boards at SJHC and SMU.

DNA Extraction

For the preparation of melanoma line DNA, cells were lysed by repeated pipetting with DNAzol® Genomic DNA Isolation Reagent (Molecular Research Center, Cincinnati, Ohio) and DNA precipitated by 100% ethanol was measured by TV spectrophotometry (25). For the preparation of melanoma tissue DNA, 8 μm sections were cut from formalin-fixed, paraffin-embedded blocks and mounted on glass slides. Sections were deparaffinized with xylene and stained with H&E for microscopic analysis to confirm tumor location and assess tissue homogeneity. Tumor and normal tissues were isolated separately by the microdissection technique under light microscopy, as previously described (26). For tissue DNA extraction, dissected tissues were digested with Proteinase K (QIAGEN, Valencia, Calif.)-containing lysis buffer at 50° C. overnight and inactivated by heat at 75° C. for 15 min. DNA was then purified with phenol-chloroform-isoamyl-alcohol (Fisher Scientific, Fairlawn, N.J.), precipitated by ethanol, and quantified by PicoGreen® dsDNA Assay Kit (Invitrogen, Carlsbad, Calif.) for double-stranded DNA (26).

mRNA Expression Analysis

The sequence of primers used for the quantitative real-time PCR (qRT) assay was as follows: RET, 5'-AACTGCAGC-GAGGAGATGTA-3' (forward) (SEQ ID NO:1) and 5'-CCG-CAAGGTCCAAGTAGTCT-3' (reverse) (SEQ ID NO:2); GFRα1, 5'-CCCTCCGGGTTAAGAACAAG-3' (forward) (SEQ ID NO:3) and 5'-GATTTCAGCTTCTGTGCCTGT-3' (reverse) (SEQ ID NO:4); GFRα3, 5'-GTGATGGCACAC-CAGAATGA-3' (forward) (SEQ ID NO:5) and 5'-CCATAG-GCTCAGGAGCAGAA-3' (reverse) (SEQ ID NO:6); glyceraldehyde-3-phosphate dehydrogenase (GAPDH), 5'-GGGTGTGAACCATGAGAAGT-3' (forward) (SEQ ID NO:7) and 5'-GACTGTGGTCATGAGTCCT-3' (reverse) (SEQ ID NO:8). The sequences of the fluorescence resonance energy transfer probes (FRET) were as follows: RET, 5'-FAM-TCTTCTCCAGGTCTTTGCTGATGTCC-BHQ-1-3' (SEQ ID NO:9); GFRα1, 5'-FAM-AAATTCCCACT-CATGTTTTGCCACC-BHQ-1-3' (SEQ ID NO:10); GFRα3, 5'-FAM-CTCTTTTCTCCTGCACGCTTCCCTT-BHQ-1-3' (SEQ ID NO:11); GAPDH, 5'-FAM-CAGCAATGCCTCCT-GCACCACCAA-BHQ-1-3' (SEQ ID NO:12), where FAM is 6-carboxyfluorescein and BHQ-1 is Black Hole Quencher 1. Reverse transcription (RT) reactions were performed with Moloney murine leukemia virus reverse transcriptase (Promega, Madison, WI) with oligo (dT) primer. The qRT assay was performed in an iCycler iQ® Real-Time Thermocycler Detection System (Bio-Rad Laboratories, Hercules, CA). 5 μl of cDNA generated from 250 ng of total RNA through RT was added to a 96-well PCR plate (Fisher, Pittsburgh, PA) in which 0.5 μM of each primer, 0.3 μM FRET probe, 1 U of AmpliTaq Gold® polymerase (Applied Biosystems, Foster City, CA), 200 M each dNTP, 4.5 mM $MgCl_2$, and PCR buffer and molecular biology grade $H_2O$ were added. Amplification of samples consisted of a precycling hold at 95° C. for 9 min, then 45 cycles of denaturation at 95° C. for 1 min, annealing for 1 min (at 55° C. for GAPDH, 58° C. for RET, 63° C. for GFRα1, 58° C. for GFRα3), and extension at 72° C. for 1 min. Specific plasmid controls for each marker were synthesized as described previously (27) and generation of calibration curves was performed with a threshold cycle of six serial dilutions of plasmid templates ($10^1$-$10^6$). To quantify the copy number, the cycle time (Ct) was interpolated from the calibration curve for each sample and mRNA copy number was calculated using Real-Time Detection System software (Bio-Rad). GAPDH was used as a control housekeeping gene and the relative mRNA copies were obtained as absolute mRNA copies of each gene / absolute mRNA copies of GAPDH (28). Each assay was performed at least twice, and mean copy numbers were used for analysis.

RETmt and BRAFmt Analysis

We used a peptide nucleic acid (PNA)-locked nucleic acid (LNA) clamp method to detect RETmt and BRAFmt polymorphism in melanoma cell lines and paraffin-embedded melanoma tissues. Detailed instruction for this method is described in previous reports (18, 24). Briefly, PCR was performed with the following primers and probes: RET (#1) 5'-CCTTCCCGGTCAGCTACTC-3' (forward) (SEQ ID NO:13), 5'-ACCCTCACCAGGATCTTGAA-3' (reverse) (SEQ ID NO:14), 5'-FAM-AGTGCCCGCCGGCCCT-BHQ-1-3' (probe) (SEQ ID NO:15), and CTTCCGGTGC-CCGCCGGCC (PNA) (SEQ ID NO:16); BRAF, 5'-CCTCA-CAGTAAAAATAGGTG-3' (forward) (SEQ ID NO:17), 5'-ATAGCCTCAATTCTTACCA-3' (reverse) (SEQ ID NO:18), 5'-FAM-CTACAGAGAAATCTCGAT-BHQ-1-3' (LNA) (SEQ ID NO:19), and CTACAGTGAAATCTCG (PNA) (SEQ ID NO:20). The PCR assay was performed using the iCycler iQ® real-time PCR Detection System. Genomic DNA ($\geq$2.5 ng) was applied to a final volume of 25 µl containing each PCR primer, probe (LNA in BRAFmt detection), PNA, each dNTP, $MgCl_2$, PCR buffer, and AmpliTa q Gold® Polymerase. PCR for RET was subjected to a precycling hold at 95° C. for 12 min, followed by 55 cycles at 94° C. for 1 min, 70° C. for 50 sec, 58° C. for 50 sec, and 72° C. for 1 min. PCR for BRAF was subjected to a precycling hold at 95° C. for 10 min, followed by 45 cycles at 95° C. for 1 min, 72° C. for 50 sec, 53° C. for 50 sec, and 72° C. for 1 min. MIAPaCa-2 and PANC-1 were used as RETmt and RETwt controls, respectively (18). DNA of ME2 and MCF7 were used as BRAFmt and BRAFwt controls, respectively (24).

Sequencing

To confirm the results of mutation analyses using the PNA clamp assay, we performed direct sequencing on representative samples, as previously described (18). RET coding regions were amplified by PCR using genomic DNA of melanoma cells and tumor tissues. The primer pair flanking exon 11 of RET genomic DNA was designed as follows: RET (#2), 5'-TACCACAAGTTTGCCCACAA-3' (forward) (SEQ ID NO:21) and 5'-GAGGGCAGGGGATCTTCC-3' (reverse) (SEQ ID NO:22). The PCR conditions were: denaturation at 94° C. for 10 min, followed by 36 cycles of 94° C. for 30 sec, 64° C. for 30 sec, and 72° C. for 30 sec, and completed with a 7 min hold at 72° C. PCR products were amplified by nested PCR with RET forward (#2) and reverse (#1) primers to increase efficiency and specificity. Since we used a reverse primer (#1) of RET for direct sequencing, the results are shown as complementary sequences. The nested PCR products were purified with QlAquick® PCR purification Kit (QIAGEN) and sequenced with GenomeLab™ DTCS quick start sequencing kit, according to manufacturer instructions (Beckman Coulter, Fullerton, CA). Sequencing fragments were applied and read with CEQ™ 8000XL Genetic Analysis System (Beckman Coulter) and analyzed by the CEQ™ 8000XL Series Genetic Analysis System Software (version 8.0).

RET IHC Analysis

Sections (5 µm) were obtained from archived formalin-fixed paraffin-embedded non-DMs and DMs. After deparaffinization in xylene and rehydration in serial-graded ethanol, endogenous peroxidase activity was quenched by 0.3% $H_2O_2$ and non-specific binding sites were blocked with 5% BSA. Sections were treated with boiling citrate buffer for heat-induced epitope retrieval. Goat anti-human polyclonal RET-specific Ab (R&D Systems, Minneapolis, Minn.), or non-specific goat IgG (Santa Cruz Biotechnology, Inc., Santa Cruz, Calif.) as a control (15 µg/ml in blocking buffer), was added to the sections for immunostaining and incubated at 4° C. for 1 hr. Ab binding sites were detected by avidin-biotin peroxidase complex solution (LSAB® Kit) and 3,3'-diaminobenzidine as a chromogen (DAKO, Carpinteria, Calif.). Counterstaining was performed with hematoxylin and assessed by light microscopy.

Western Blotting

Cells were washed twice with ice-cold phosphate-buffered saline (PBS) and dissolved in solubilizing buffer (pH 7.5, 20 mM Tris-HCL, 12.5 mM β-glycerophosphate, 2 mM EGTA, 10 mM NaF, 1 mM benzamide, 1% NP-40, 1 mM $Na_3VO_4$, 1× protease inhibitor mix) after treatment with 25 µg human recombinant GDNF (Chemicon International, Temecula, Calif.). Each aliquot of protein (10 µg) was subjected to Western blotting analysis. After electrophoresis on 12.5% polyacrylamide gels, the protein was transblotted to Hybond™-P (Amersham Life Sciences, Inc., Arlington Heights, Ill.) in transfer buffer (192 mM glycine, 25 mM Tris, 2.5 mM SDS, and 10% methanol). The blots were blocked with 5% non-fat dry milk, and then incubated with anti-ERK 1/2 rabbit polyclonal Ab, or anti-phosphorylated ERK 1/2 rabbit polyclonal Ab (1:1000, Phosphoplus® p44/42 MAP Kinase (Thr202/Tyr204) Antibody kit, Cell Signaling Technology, Danvers, Mass.), and then incubated with an horse radish peroxidase (HRP)-conjugated anti-rabbit IgG Ab (1:2000, Cell Signaling Technology). As for Western blotting of Akt, anti-Akt rabbit polyclonal Ab, or anti-phosphorylated Akt rabbit polyclonal Ab (1:500, Phosphoplus® Akt (Ser473) Antibody Kit, Cell Signaling Technology) and a secondary Ab, HRP-conjugated anti-rabbit IgG Ab (1:1000), were used. Subsequently, the blots were developed with ECL Plus Western blotting Detection system (GE Healthcare Life Sciences, Piscataway, N.J.) according to the manufacturer instructions.

Cell Proliferation Assay

Cell proliferation 48 and 72 hrs after GDNF treatment (5, 25 or 50 ng/ml, dissolved in water) in serum-free medium was analyzed by 3-(4,5-dimethylthiazol-2-yl)-2,5-diphenyltetrazolium bromide (MTT) and direct cell counting with a light microscope, respectively. MTT (0.4 mg/ml, Sigma-Aldrich, St. Louis, Mo.) was added into culture wells after washing with PBS. The converted dye was dissolved with DMSO 2 hrs after incubation at 37° C. and the absorbance was measured at a wavelength of 550 nm with a microplate reader (Bio-Rad). For cell counting, cells were harvested after washing with PBS and the number of cells was counted using a hemocytometer under a microscope. In blocking assays, cells were pre-treated with 10 µM of a MEK1 inhibitor, PD98059 (Cell Signaling Technology), or 100 nM of a PI3K inhibitor, wortmannin (Cell Signaling Technology), for 60 min before treatment of GDNF as indicated in the instructions from the company, and followed by 25 ng/ml of GDNF treatment for 72 hrs. To avoid the effect of the delivery agent on cells, PD98059 and wortmannin were dissolved in PBS, and the same amount of PBS was added to control (GDNF(−)) and GDNF-treated cells.

Migration Assay

Migration ability of the melanoma cells was determined with a modified technique using a Transwell® chamber with a microporous membrane (membrane diameter 6.5 mm, pore size 8 µm, CORNING, Corning, N.Y.) (29). Melanoma cells were seeded in the upper chamber with RPMI 1640 culture medium (Invitrogen) with 2% fetal bovine serum (FBS). The lower chamber contained RPMI 1640 culture medium with 2% FBS and 5 or 25 ng/ml of GDNF. The cells that migrated through the membrane and adhered to the bottom of lower chamber were fixed with 80% ethanol and stained with hematoxylin 48 hrs after incubation at 37° C. The number of stained cells was counted in a total of 5 fields under a microscope with 200× magnification. In blocking assays, cells were pre-treated with wortmannin (100 nM) for 60 min before treatment of GDNF as indicated in the instructions from the company and followed by treatment with 25 ng/ml GDNF for 48 hrs. To avoid the effect of the delivery agent on cells, wortmannin was dissolved in PBS, and the same amount of PBS was added to control (GDNF(−)) and GDNF-treated cells.

Invasion Assay

Invasion ability of the melanoma cells was analyzed using QCM™ Collagen-based Invasion Assay MILLIPORE, Billerica, Mass.), as described in previous reports (27, 29). Cells were seeded in the upper chamber with RPMI 1640 culture medium (Invitrogen) with 2% FBS containing GDNF. The lower chamber contained RPMI 1640 culture medium with 5% FBS and GDNF with same concentration as the upper chamber (25 ng/ml). Cells invading the collagen-coated membrane were fixed and stained 60 hrs after incubation at 37° C. using reagents provided by MILLIPORE, according to the manufacturer's instructions. Stained cells were dissolved with a provided reagent and measured at a 550 nm wavelength with a microplate reader (Bio-Rad). In the blocking assay, cells were pre-treated with 1 µg/ml of a goat anti-human polyclonal RET-specific Ab, which binds to the extracellular domain of RET (R&D Systems), or 1 µg/ml control goat IgG (Santa Cruz Biotechnology) as a control 60 min before treatment with GDNF and followed by treatment with 25 ng/ml GDNF for 60 hrs.

RNA Interference

A siRNA against RET and non-specific control siRNA were designed and synthesized by Dharmacon, Inc. (Lafayette, Colo.). RETmt melanoma cells (ME1) were seeded into a 96 well plate (1×10$^4$ cells/well) without antibiotics. The siRNA was transfected with DharmaFECT™ 1 Transfection Reagent. The suppression of RET mRNA was confirmed with qRT assay 24 and 48 hrs after transfection. Each assay using siRNA was performed at least three times and the mean values were employed for analysis.

Actin Polymers Staining by Alexa Fluor® 568 Phalloidin

Melanoma cells were seeded in BD BioCoat™ CultureSlides (BD Biosciences, San Jose, Calif.). Cells were washed twice with PBS and fixed with 3.7% formaldehyde solution in PBS for 10 min at room temperature after a 48 hr incubation with GDNF (10 ng/ml) at 37° C. Fixed cells were stained with 1 U/200 µl of PBS Alexa Fluor® 568 phalloidin (Invitrogen) for 20 min at room temperature. After washing twice with PBS, actin polymers were observed using fluorescence microscopy with 400× magnification.

Biostatistical Analysis

The correlation of RETmt and BRAFmt frequency in DMs and non-DMs was assessed by the Chi squared test. In functional assays, statistical analyses were performed by Wilcoxon's signed ranks test and unpaired t test. Results are shown as mean±SD. A P-value of <0.05 (two-tailed) was considered significant. All statistical analyses were done using JMP® software (SAS, Cary, N.C.).

Results

Expression of RET, GFRα1, and GFRα3

Figure 2A:
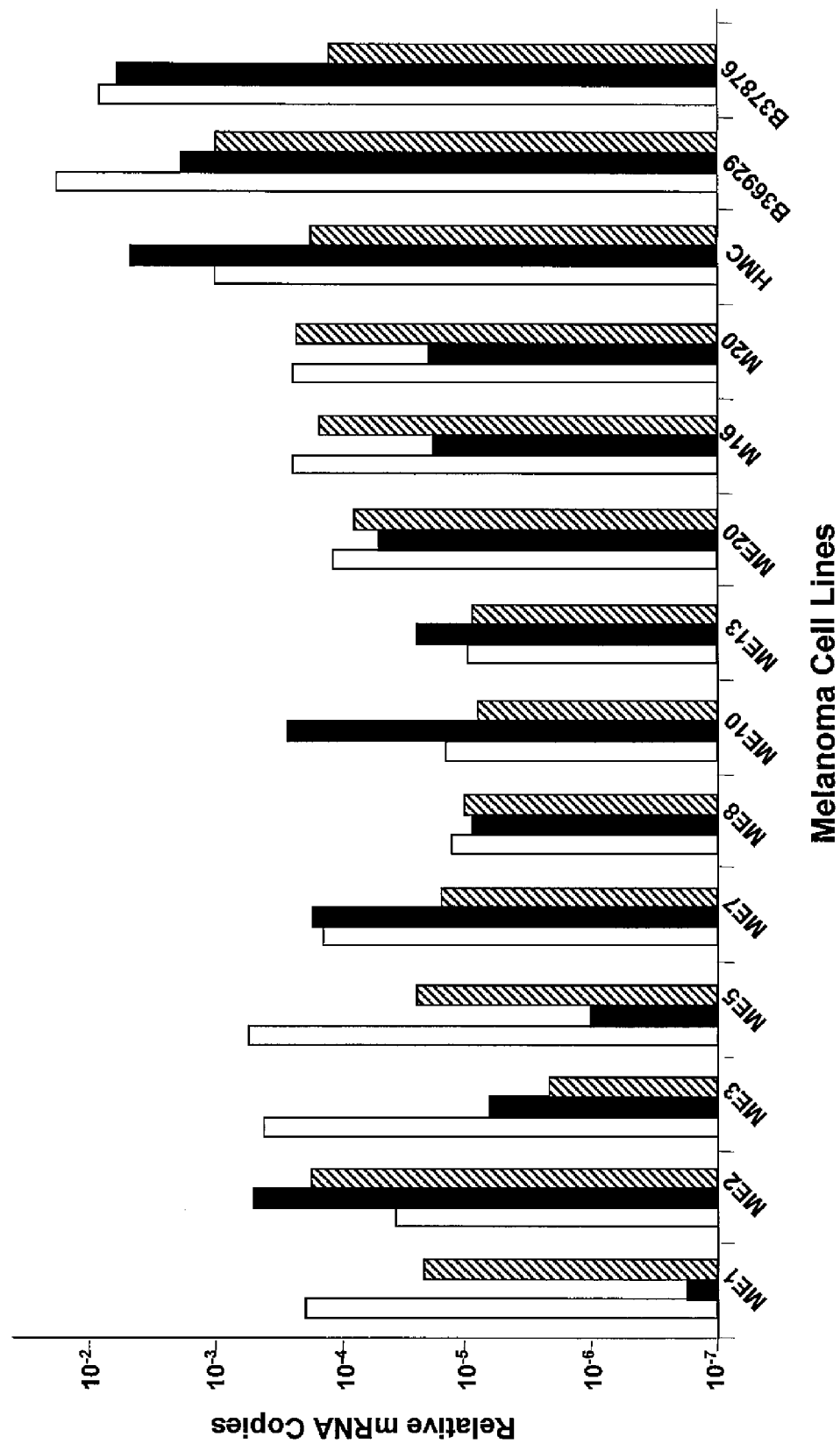
FIG. 2. mRNA expression of RET, GFRα1 and GFRα3 by real-time quantitative PCR in melanoma cell lines. (A) shows the mRNA expression of ☐RET, ■GFRα1, and ▨GFRα3, respectively. Human normal melanocytes (HMC) and normal brain tissues (B36929, B37876) were used as controls. Copy numbers of mRNA were normalized using mRNA copy numbers of the house-keeping gene, GAPDH. (B) RET expression detected by immunohistochemical staining in desmoplastic melanoma (a, c), non-desmoplastic melanoma (d, f) and respective negative controls (b, e). Anti-RET Ab and control show staining with anti-RET specific antibody and non-specific goat IgG, respectively. The scale bars represent 50 μm in length.
Figure 2B:
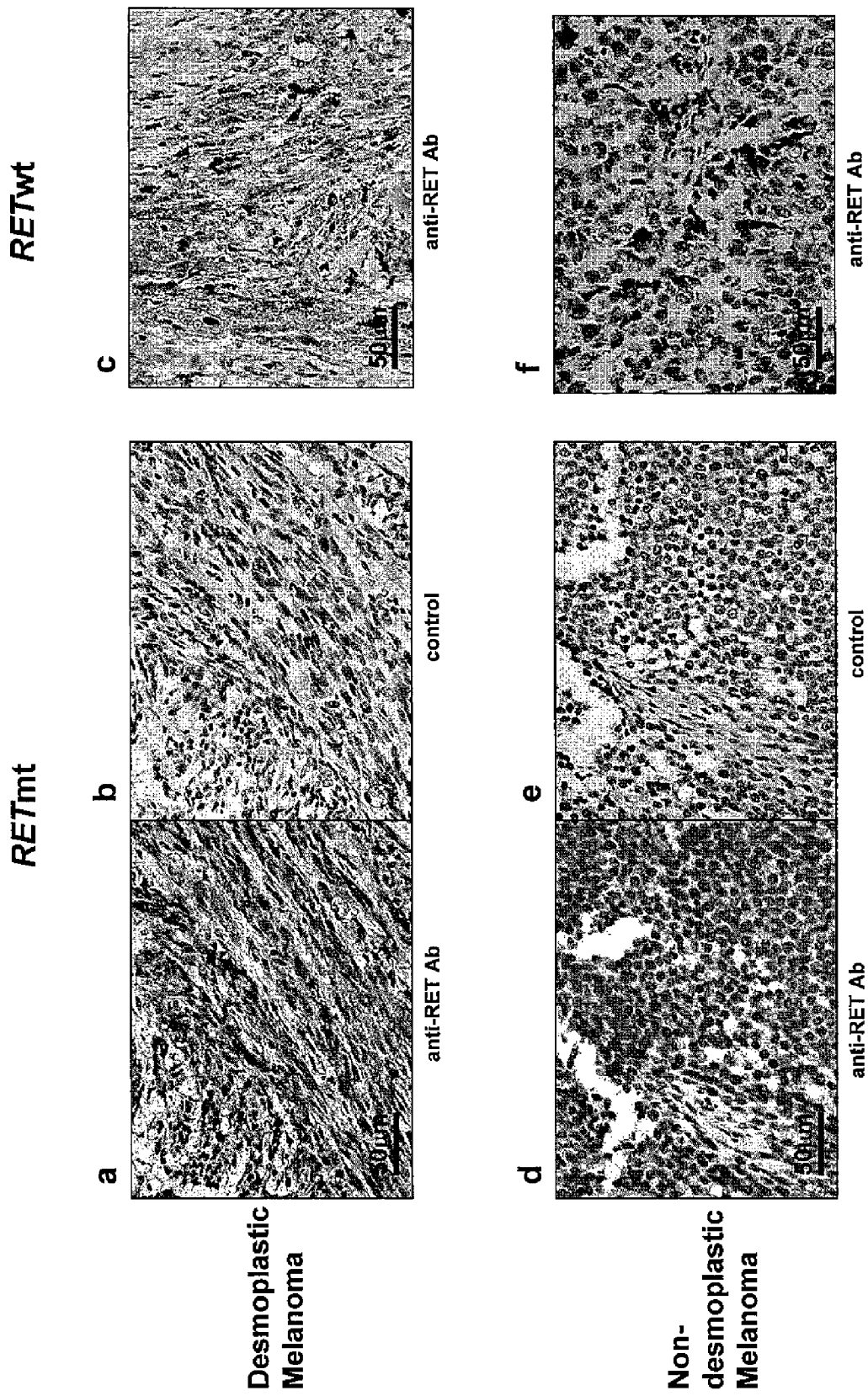

To confirm the existence of GDNF-RET signaling pathway in melanoma, the mRNA expressions of RET, GFRα1, and GFRα3 were analyzed in melanoma cell lines using quantitative real-time PCR (qRT). All melanoma lines expressed mRNA of RET, GFRα1, and GFRα3 (FIG. 2A). The patterns of mRNA expression were independent of RETmt presence (RETmt status in melanoma lines are shown below). Normal human brain tissues (B36929, B37876) served as positive controls for GFRα1 and GFRα3 mRNA, and normal human melanocytes (HMC) were used as a reference control line. Immunohistochemistry (IHC) was performed to confirm the expression of the RET receptor in melanoma tissues. IHC analysis of both non-DMs and DMs demonstrated that RET was expressed independently of RETmt status in melanoma tissue (FIG. 2B). There were no significant increases in RET receptor protein expression in RET wild-type (RETwt) versus RETmt melanomas.

Analyses of RETmt and BRAFmt

Figure 6:
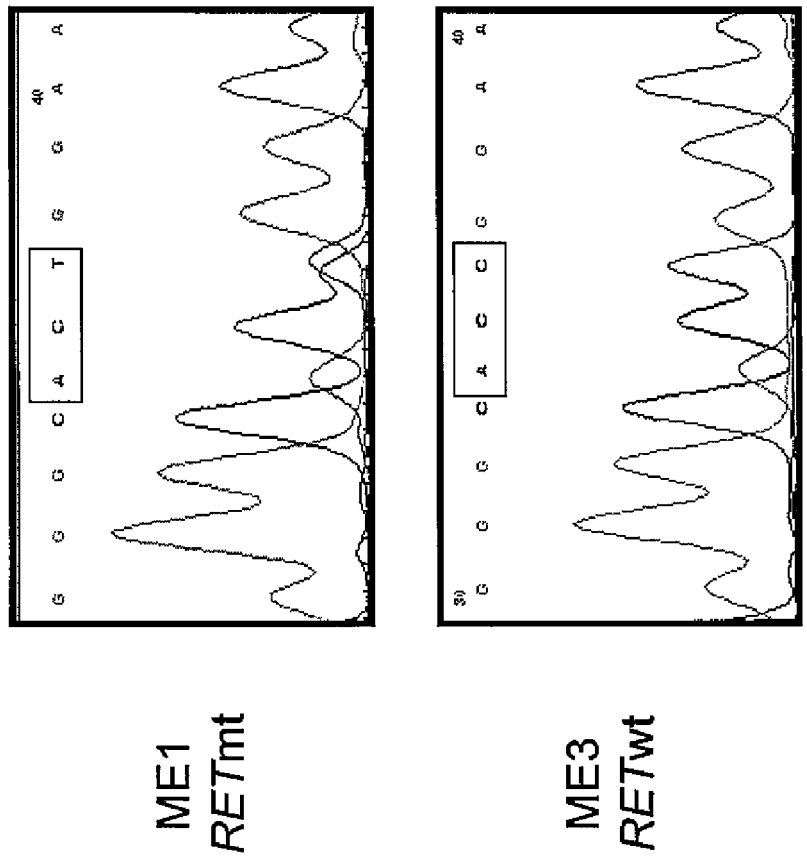
FIG. 6. Representative direct sequencing for RET in melanoma cells. Lower panel shows sequence of wild type as ACC. Upper panel shows RETmt as ACT. Since a reverse primer (#1) of RET for direct sequencing was used, these results are shown as complementary sequences of GGT (wt) and AGT (mt).

Since BRAF is a component of the downstream signaling pathway of RET, and BRAFmt may enhance the signaling activation of RET (10, 19), we investigated RETmt (RET G691S mutation), BRAFmt (BRAF V600E mutation), RETwt, and BRAF wild-type (BRAFwt) in melanoma lines. Mutant and wild-type melanoma lines were determined by a peptide nucleic acid (PNA) clamp PCR assay for both RETmt (G691S) and BRAFmt (V600E): ME1 was RETmt and BRAFmt. ME5 and ME7 were RETmt and BRAFwt. ME3 and ME10 were RETwt and BRAFwt. M1G was RETwt and BRAFmt. For RET mutation detection, the results were also validated using direct sequencing (FIG. 6). The sequence of RETwt was ACC, while RETmt was ACT, indicating a single polymorphic nucleotide change (GGT→AGT).

RETmt and BRAFmt DNA analyses were performed on histopathologically-verified surgical tissues of non-DMs (n=71) and DMs (n=70). The frequency of RETmt was about twice as high in DMs (61%) as compared to non-DMs (31%) (P<0.001, Table 1). BRAFmt was significantly (P<0.001) higher in non-DM (39%) than DM tumors (11%). The reduced frequency of BRAFmt in DMs was striking and has important implications as to the role of BRAFmt in sun-exposed sites of cutaneous melanomas overall. Details of RETmt and BRAFmt analysis of primary and metastatic tumors were assessed (Table 1). BRAFmt was detected more frequently in metastatic than in primary tumors in both non-DMs and DMs. However, there was no similar relation in RETmt between primary and metastatic melanomas of both non-DMs and DMs.

TABLE 1

RETmt and BRAFmt in Non-desmoplastic Cutaneous and Desmoplastic Melanomas

| Melanoma type | | RETmt | BRAFmt |
|---|---|---|---|
| Cutaneous | All (n = 71) | 31% | 39% |
| | Primary (n = 35) | 37% | 29% |
| | Metastatic (n = 36) | 25% | 50% |
| Desmoplastic | All (n = 70) | 61% | 11% |
| | Primary (n = 51) | 63% | 10% |
| | Metastatic (n = 19) | 58% | 16% |

RETmt was assessed in paired tumor-free normal skin from the RETmt samples of non-DM (n=14) and DM (n=25). In non-DMs, only 7 of 14 matched normal tissue (50%) had RETmt, suggesting an acquired somatic mutation in the melanomas. In DMs, 21 of 25 normal tissue (84%) had RETmt, implying that RETmt is a predominantly hereditary polymorphism in DMs.

GDNF Effect on Proliferation

Figure 3A:
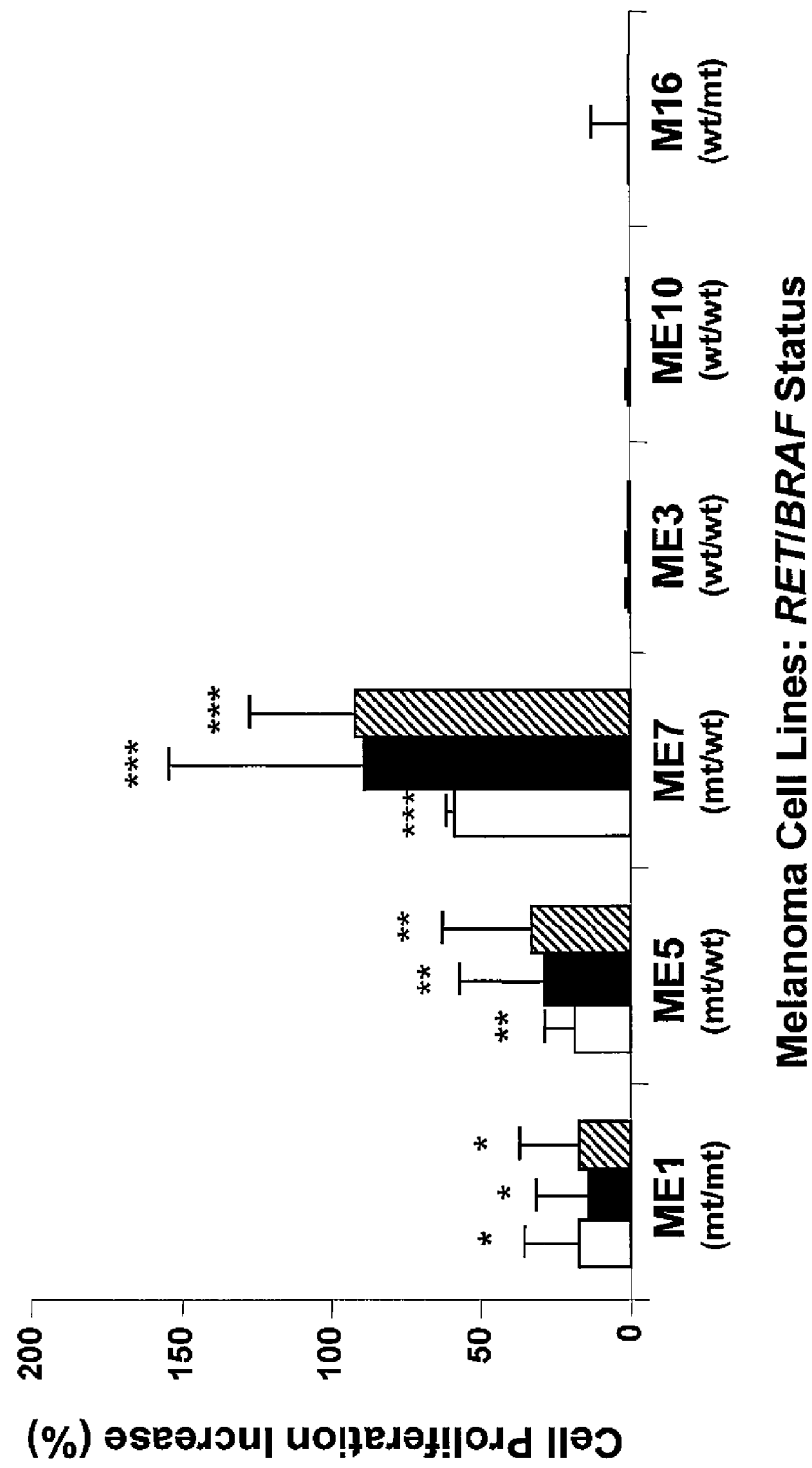
FIG. 3. Cell proliferation by GDNF. (A) Proliferation of melanoma cells was analyzed using the MTT assay. Cells were treated with ☐5 ng/ml, ■25 ng/ml, or ▨50 ng/ml of GDNF in serum-free medium for 48 hrs. Columns show increase in percentage over each delivery agent-treated control cell. *, , *, $P<0.05$ vs each control. Columns without asterisks indicate no significant change compared to each control. (B) Proliferation of melanoma cells was analyzed using direct cell counting. In the cell counting assay, cells were treated with 50 ng/ml of GDNF in serum-free medium for 72 hrs. Columns show increase in percentage over each delivery agent-treated control cell. *, , *, $P<0.05$ versus each control. Columns without asterisks indicate no significant change compared to each control. (C) In the blocking assay, ME7 cells were pretreated with PD98059 or wortmannin for 60 min before 25 ng/ml of GDNF treatment for 72 hrs. Columns show increase (fold) compared to delivery agent-treated control (GDNF(−)). *, , *, $P<0.05$. (D) mRNA expression of RET suppressed by RET specific siRNA 24 (left panel) and 48 (right panel) hrs after transfection in ME1. *, **, $P<0.05$. Copy numbers of RET mRNA were normalized using mRNA copy numbers of the house-keeping gene, GAPDH, and expressed as relative copies. (F) GDNF (25 ng/ml) was administrated to ME1 48 hrs after transfection of RET specific siRNA or non-specific siRNA. Columns show increase (fold) compared to delivery agent-treated control (GDNF(−)). *, **, $P<0.05$.
Figure 3B:
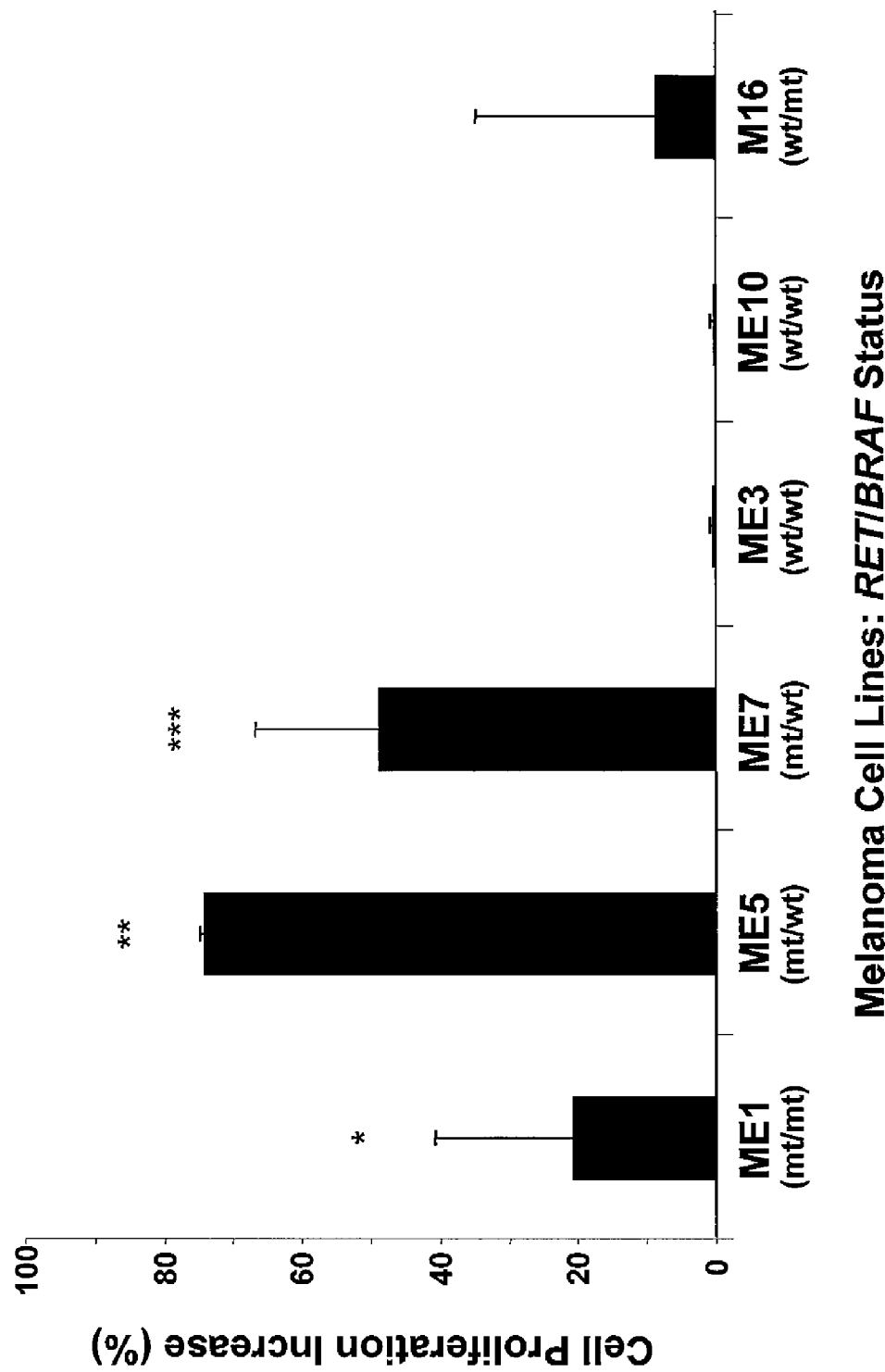

The effects of RETmt and BRAFmt on GDNF-induced cell proliferation were analyzed by a colorimetric MTT assay. A 48-hr exposure to GDNF enhanced proliferation of RETmt melanoma cells but not RETwt melanoma cells (FIG. 3A). GDNF did not differentially enhance the proliferation of BRAFmt and BRAFwt cells (FIG. 3A). MTT assay results were confirmed by a direct cell-counting assay performed 72 hr after administration of GDNF (FIG. 3B). We selected 25 ng/ml of GDNF as the optimal working dose for assessing cell proliferation (FIG. 3A).

Figure 3C:
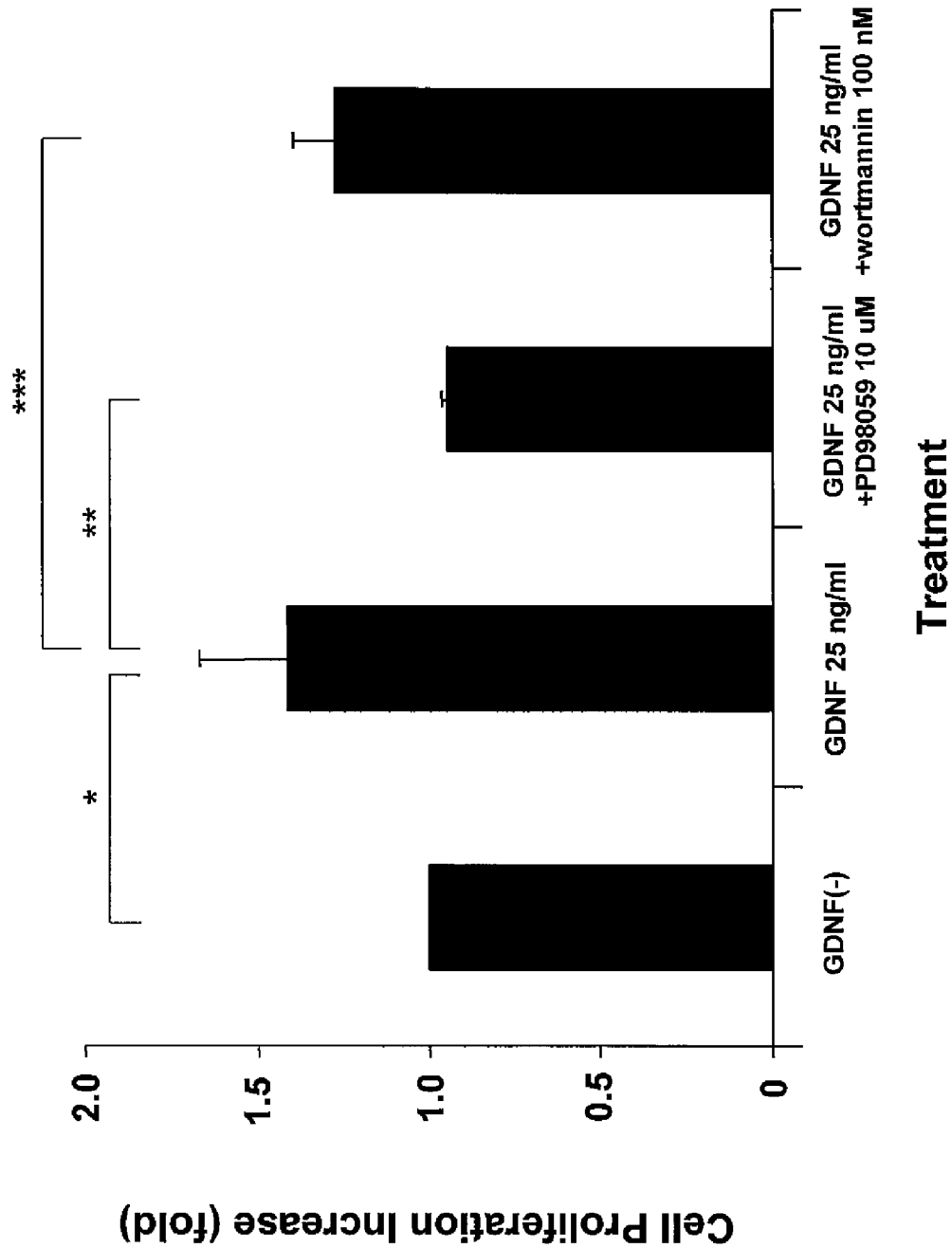
Figure 3D:
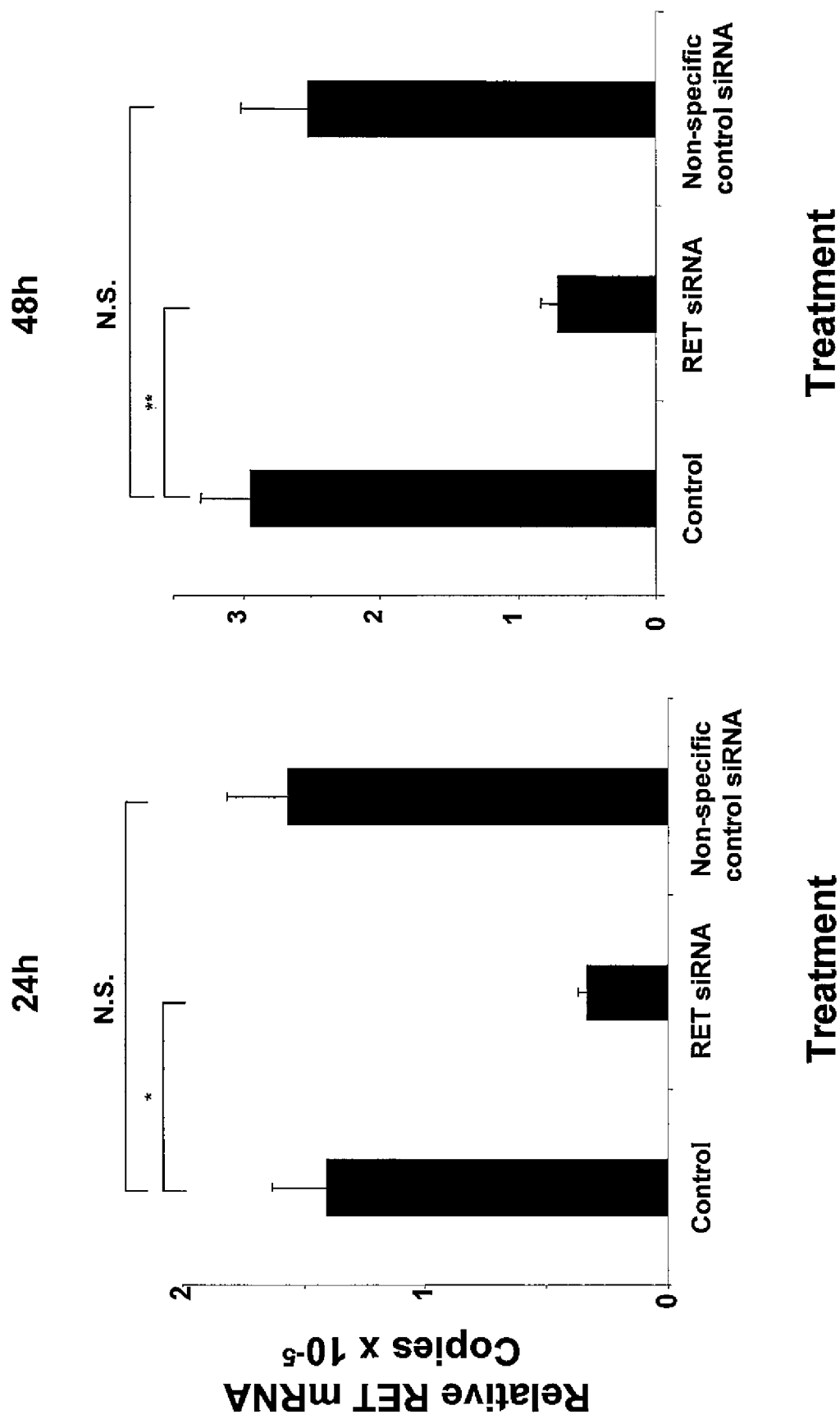
Figure 3E:
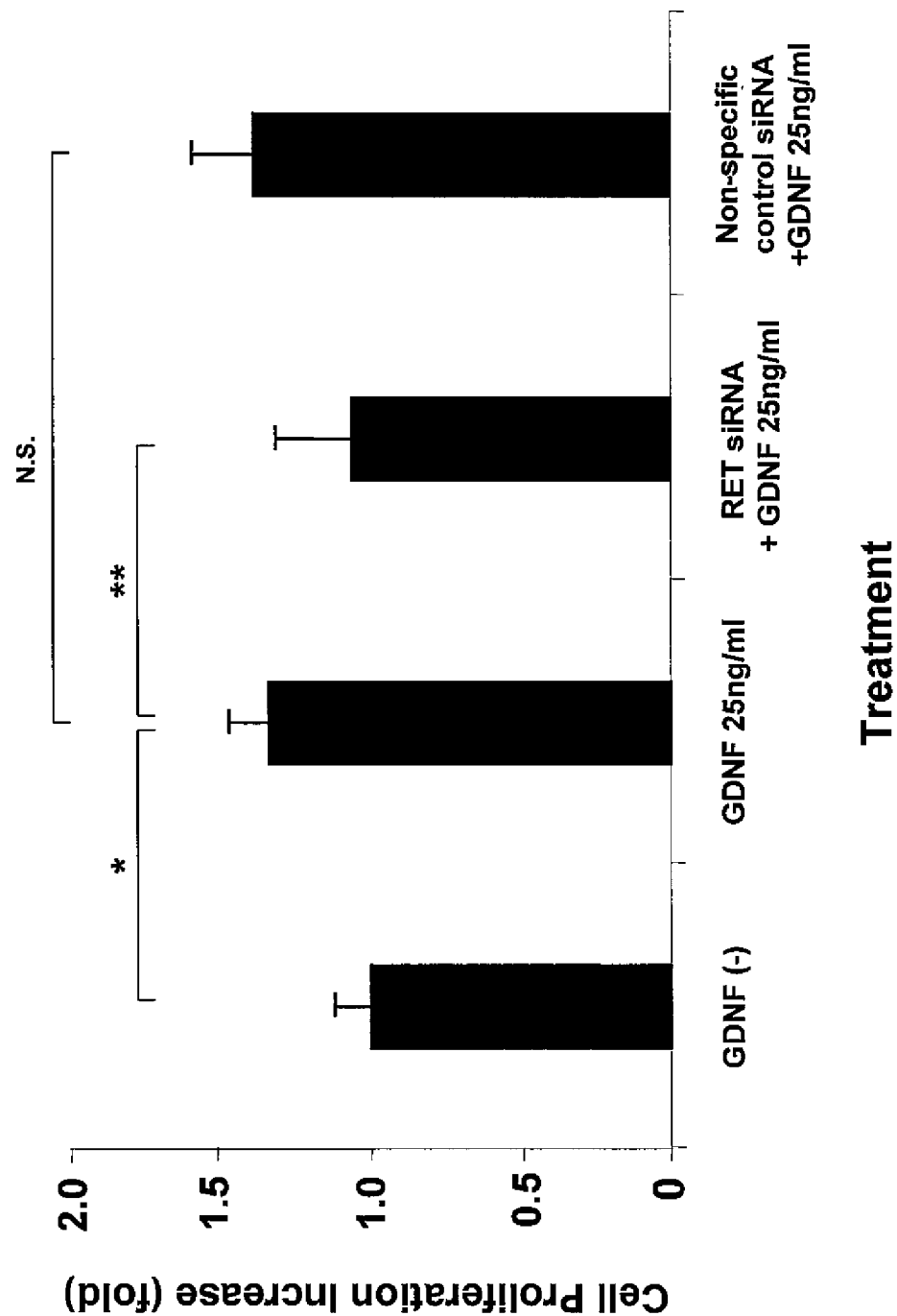

The pathway for GDNF-induced proliferation was examined by treating cells with agents that block components of the two important downstream pathways for RET signaling of cell proliferation. PD98059 is a MEK1 inhibitor that targets the RET-RAS-ERK pathway. Wortmannin is a PI3K inhibitor that targets the RET-PI3K-Akt pathway (FIG. 1). PD98059 treatment completely suppressed GDNF-induced proliferation. Wortmannin partially suppressed GDNF-induced proliferation in ME7 (RETmt/BRAFwt) (FIG. 3C). This suggested that the RET-RAS-BRAF-ERK signaling pathway plays a more predominant role than the RET-PI3K-Akt pathway with respect to GDNF-induced cell proliferation in RETmt melanoma cells. To exclude the possibility that cross-talk signaling pathways via other receptors are involved in GDNF activation of RET signaling pathways, we transfected small interfering RNA (siRNA) against RET in RETmt cells (ME1) and cell proliferation induced by GDNF was assessed using the MTT assay. The RET siRNA significantly ($P<0.05$) reduced expression of RET mRNA 24 and 48 hrs after transfection by 77% and 76%, respectively compared to the non-treated cells (control) (FIG. 3D). The non-specific siRNA control did not significantly affect mRNA expression of RET (FIG. 3D). RET siRNA significantly ($P<0.05$) suppressed over 80% of cell proliferation induced by GDNF (25 ng/ml) 48 hrs after stimulation, whereas non-specific control siRNA significantly did not (FIG. 3E). These results suggest that cross-talk signaling through other receptors is not involved in the RET pathways activated by GDNF.

GDNF Effect on RETmt Cell Migration and Invasion

Figure 4A:
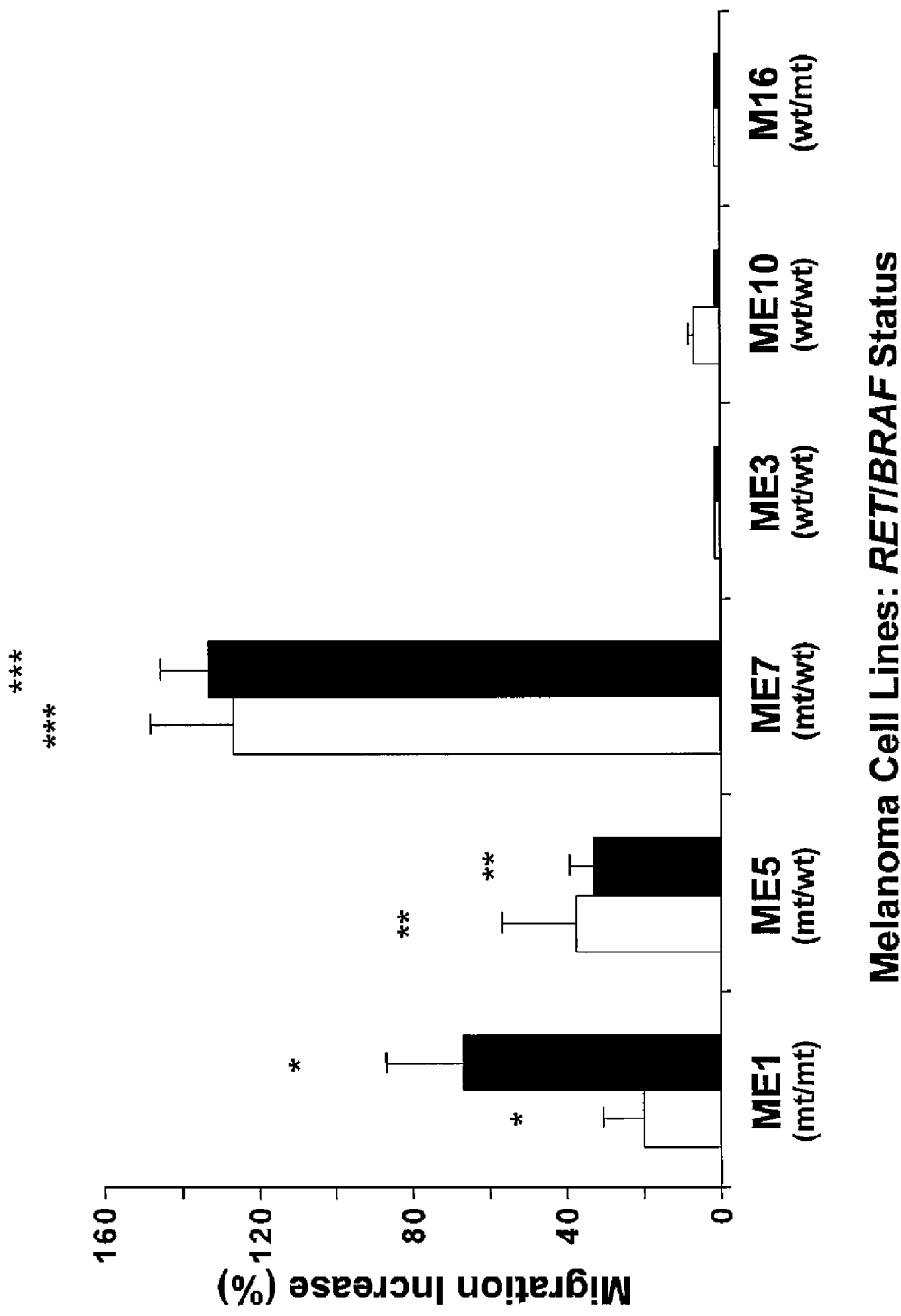
FIG. 4. Cell migration and invasion by GDNF. (A) Migration of melanoma cells was analyzed using a Transwell® chamber. Cells were treated with ☐5 ng/ml or ■25 ng/ml GDNF for 48 hrs. Columns show increase in percentage over each delivery agent-treated control cell. *, , *, $P<0.05$ versus each control. Columns without asterisks indicate no significant change compared to each control. (B) Invasion of melanoma cells was analyzed using the QCM™ Collagen-based Invasion Assay. Cells were treated with 25 ng/ml of GDNF for 60 hrs. Columns show increase in percentage over each delivery agent-treated control cell. *, **, $P<0.05$ versus each control. Columns without asterisks indicate no significant change compared to each control. (C) In the blocking assay, ME5 cells were pre-treated with wortmannin for 60 min before 25 ng/ml of GDNF treatment for 48 hrs. Columns show increase (fold) of migration compared to delivery agent-treated control (GDNF(−)). *, **, $P<0.05$. (D) In the blocking assay, ME1 cells were pre-treated with RET specific Ab or non-specific anti-goat IgG (control) for 60 min before 25 ng/ml of GDNF treatment for 60 hrs. Columns show increase (fold) of invasion compared to delivery agent-treated control (GDNF(−)). *, **, $P<0.05$.
Figure 4B:
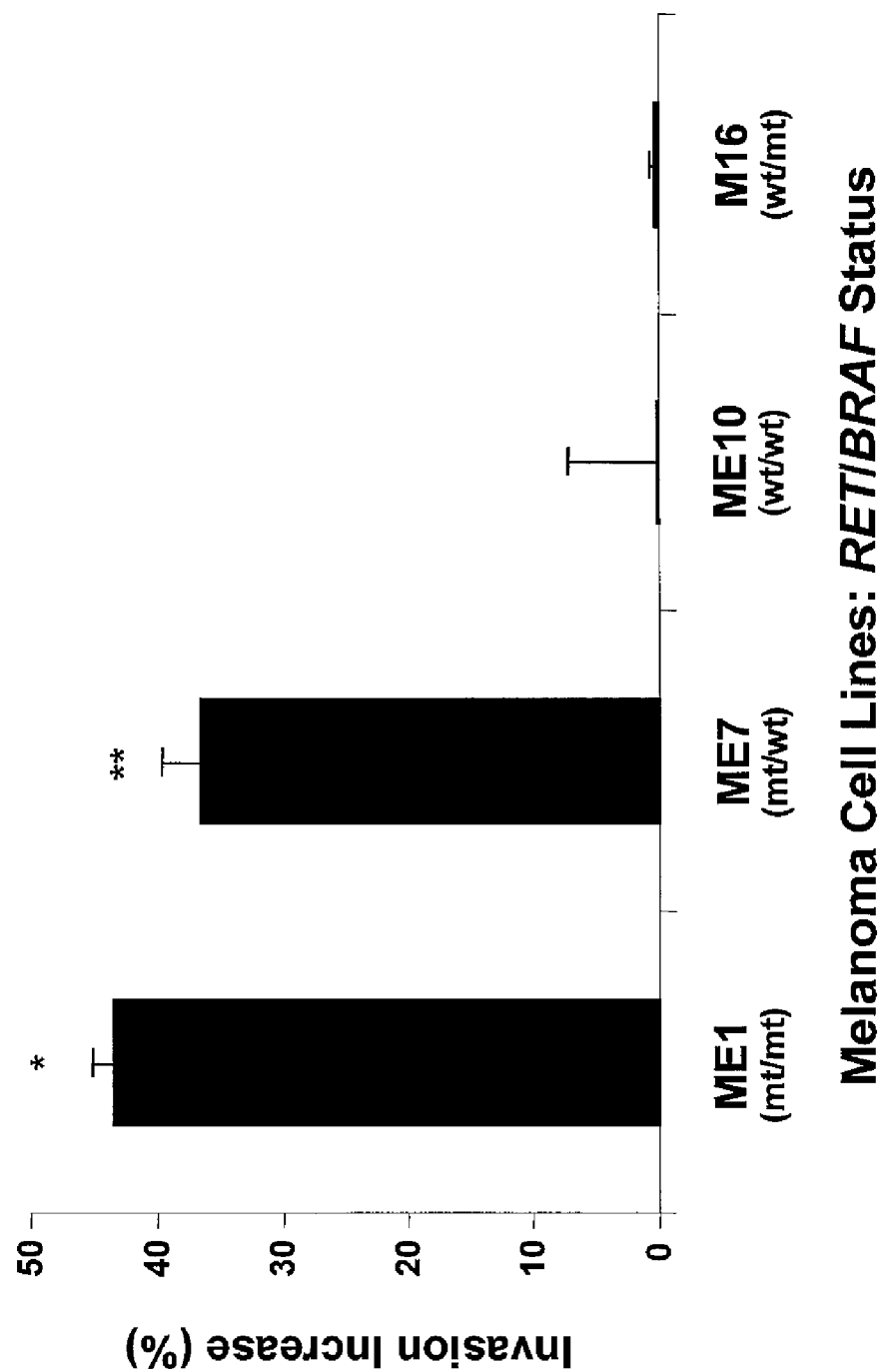
Figure 4C:
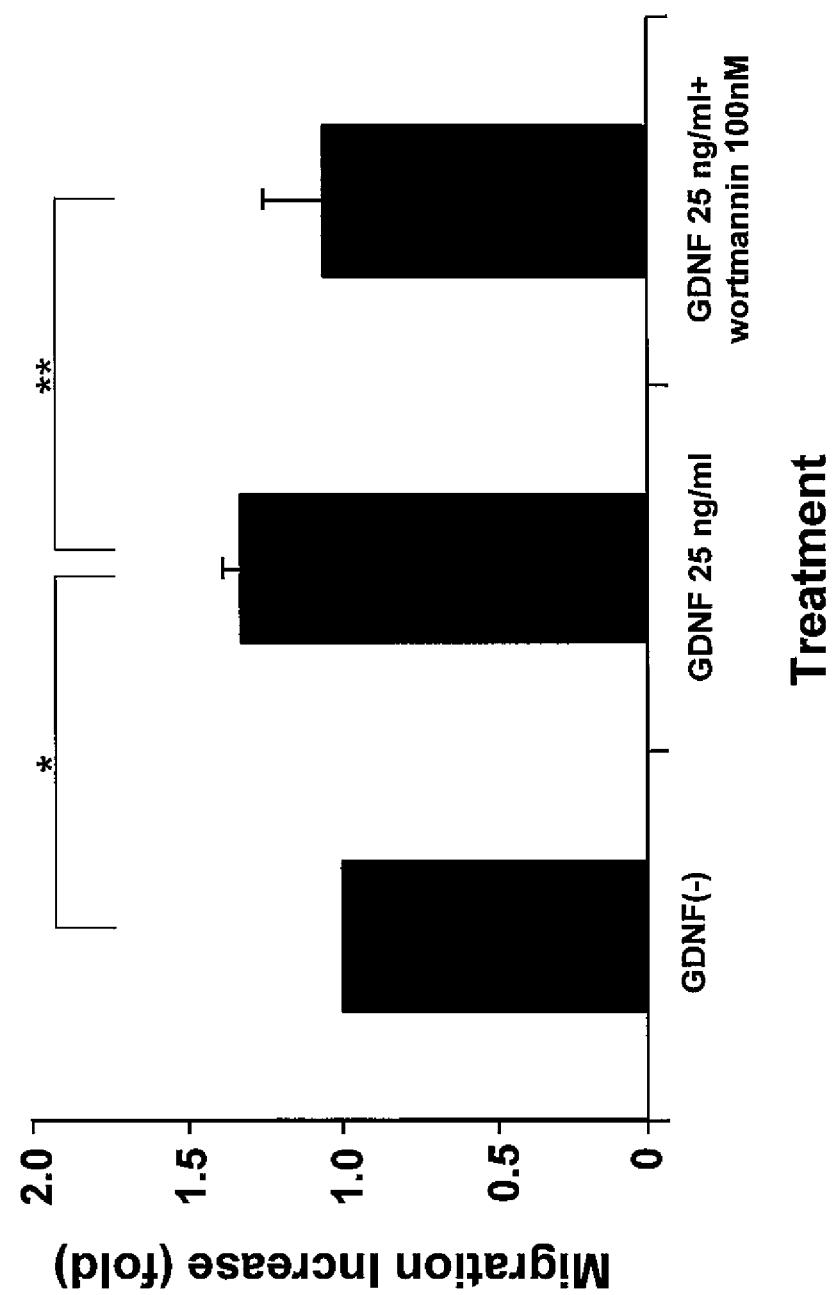
Figure 4D:
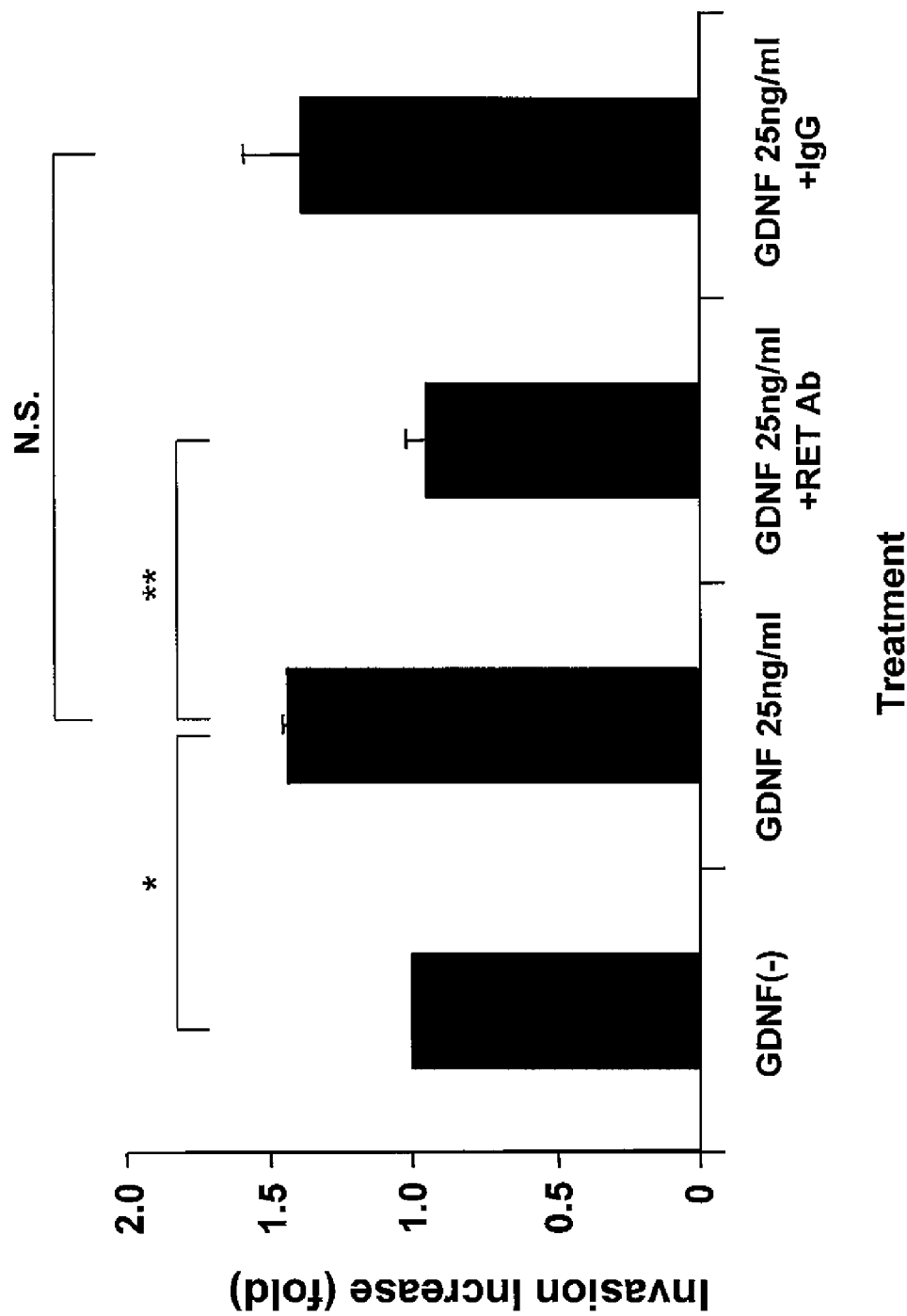
Figure 5:
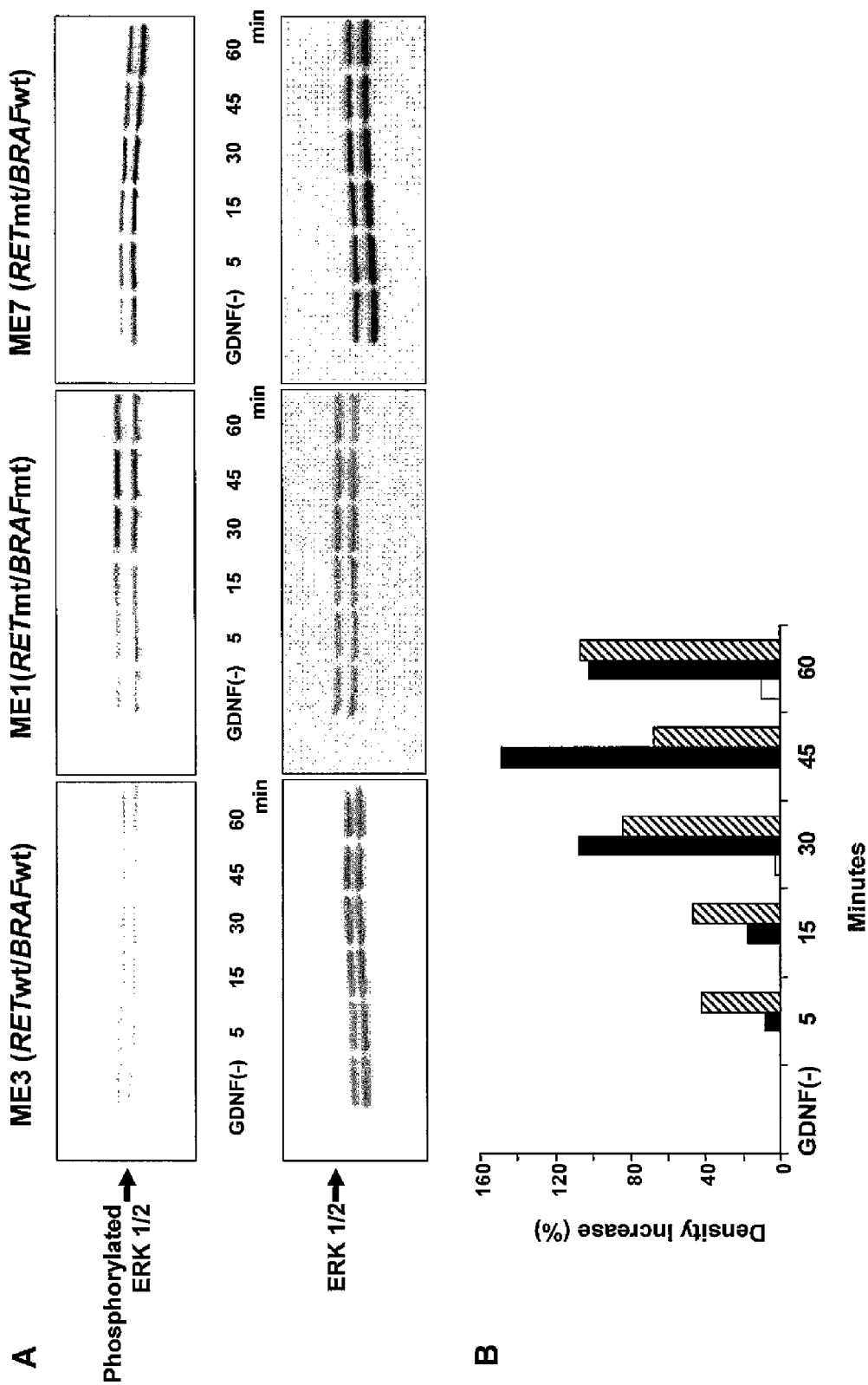
FIG. 5. Phosphorylation of ERK 1/2 and Akt by GDNF. (A) Protein expression of ERK1/2 and phosphorylated ERK 1/2 after stimulation of GDNF in ME3 (RETwt/BRAFwt), ME1 (RETmt/BRAFmt), and ME7 (RETmt/BRAFwt), respectively. Cells were treated with 25 ng/ml of GDNF for 5, 15, 30, 45, or 60 minutes. Non-phosphorylated ERK 1/2 was used as a loading control. (B) Increase (%) in blot density of phosphorylated ERK 1/2 over each delivery agent-treated control (GDNF(−)); ☐ME3; ■ME1; ▨ME7. (C) Protein expression of Akt and phosphorylated Akt after stimulation of GDNF in ME3 (RETwt/BRAFwt), ME1 (RETmt/BRAFmt), and ME5 (RETmt/BRAFwt), respectively. Cells were treated with 25 ng/ml of GDNF for 5, 15, 30, 45, or 60 minutes. Non-phosphorylated Akt was used as the loading control. (D) Increase (%) of blots density of phosphorylated Akt over each delivery agent-treated control (GDNF(−)). ☐ME3; ■ME1; ▨ME5.
Figure 5:
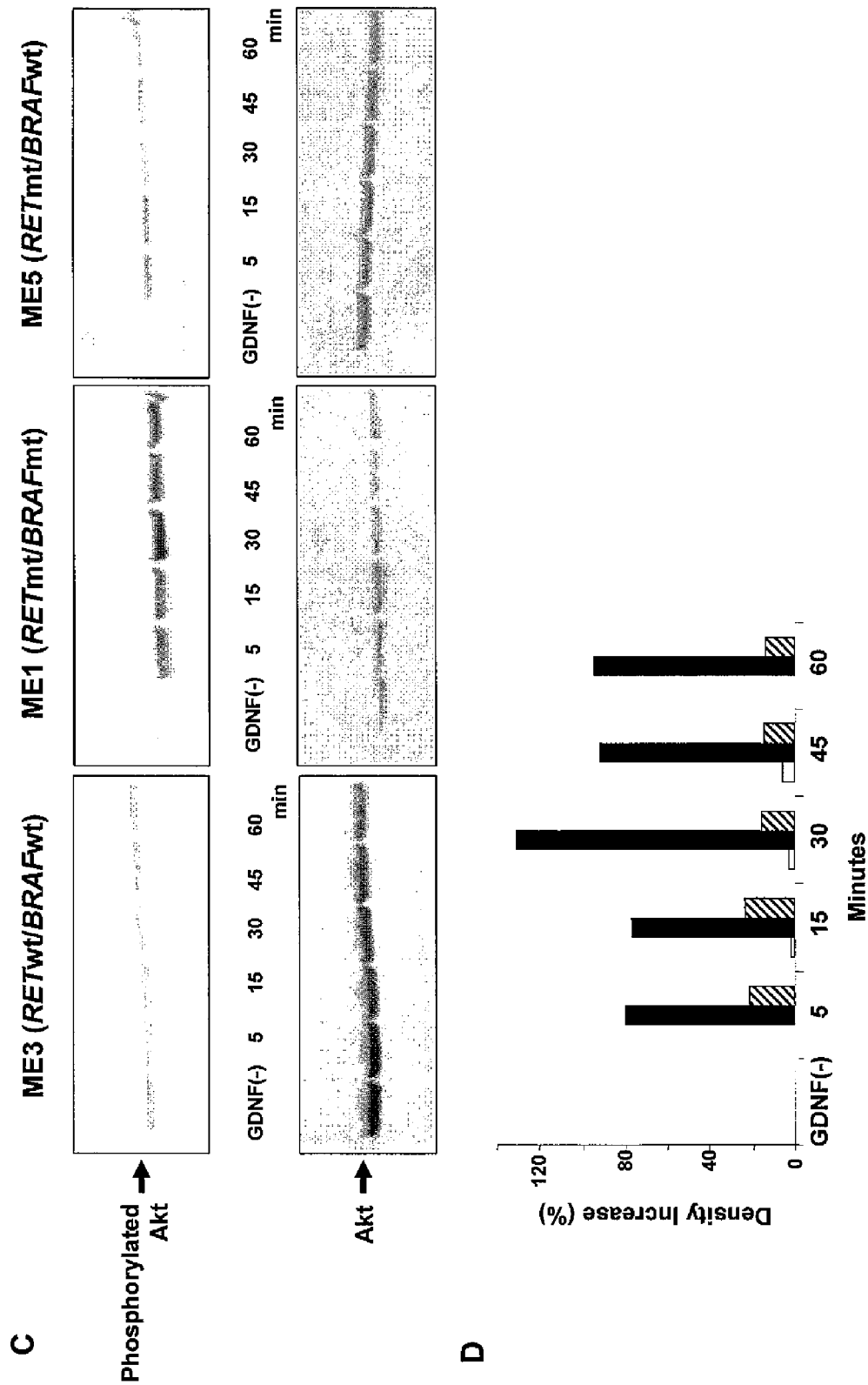

Next, to assess whether RETmt affects cell migration or invasion induced by GDNF via the RET-PI3K pathway, migration and invasion assays were performed using microporous-membrane chambers and collagen-coated chambers, respectively. RETmt cells showed more vigorous migration and invasion than RETwt cells after GDNF stimulation (FIG. 4A, B). BRAFmt cells demonstrated no effect on cell migration and invasion after GDNF treatment (FIG. 4A, B). Wortmannin strongly suppressed migration induced by GDNF in ME5 (RETmt/BRAFwt) (FIG. 4C). These results suggest that the RET-PI3K signaling pathway plays an important role in cell motility induced by GDNF in RETmt melanoma cells. The invasion ability of ME1 (RETmt/BRAFmt) enhanced by GDNF was significantly suppressed with anti-RET-specific antibody (Ab) (FIG. 4D). Non-specific purified anti-goat IgG, used as a control, did not show any effects on cell invasion induced by GDNF (FIG. 4D). These results confirmed that cross-talk signaling pathways via other receptors are not significantly involved in GDNF activation of RET signaling pathways.

Phosphorylation of ERK1/2 and Akt by GDNF

To assess the effect of RETmt activation on downstream factors of the RET signaling pathway, we analyzed whether RETmt or BRAFmt enhanced phosphorylation of ERK1/2 and Akt using Western blotting, since RET-RAS-ERK and RET-PI3K-Akt are the major signaling pathways activated by GDNF stimulation leading to cell proliferation (10). In a representative cell line, ME3 (RETwt/BRAFwt), GDNF showed weak phosphorylation of ERK1/2 and Akt. In contrast, GDNF strongly phosphorylated ERK1/2 and Akt within 15 min after treatment in ME1 (RETmt/BRAFmt), ME7 or ME5 (RETmt/BRAFwt), and phosphorylation of ERK1/2 and Akt lasted for 60 min (FIGS. 5A-D). These results confirm that RETmt enhanced the response of both RET-RAS-BRAF-ERK and RET-PI3K-Akt signaling pathways after GDNF stimulation.

Actin Polymerization in Melanoma Cells by GDNF

Figure 7:
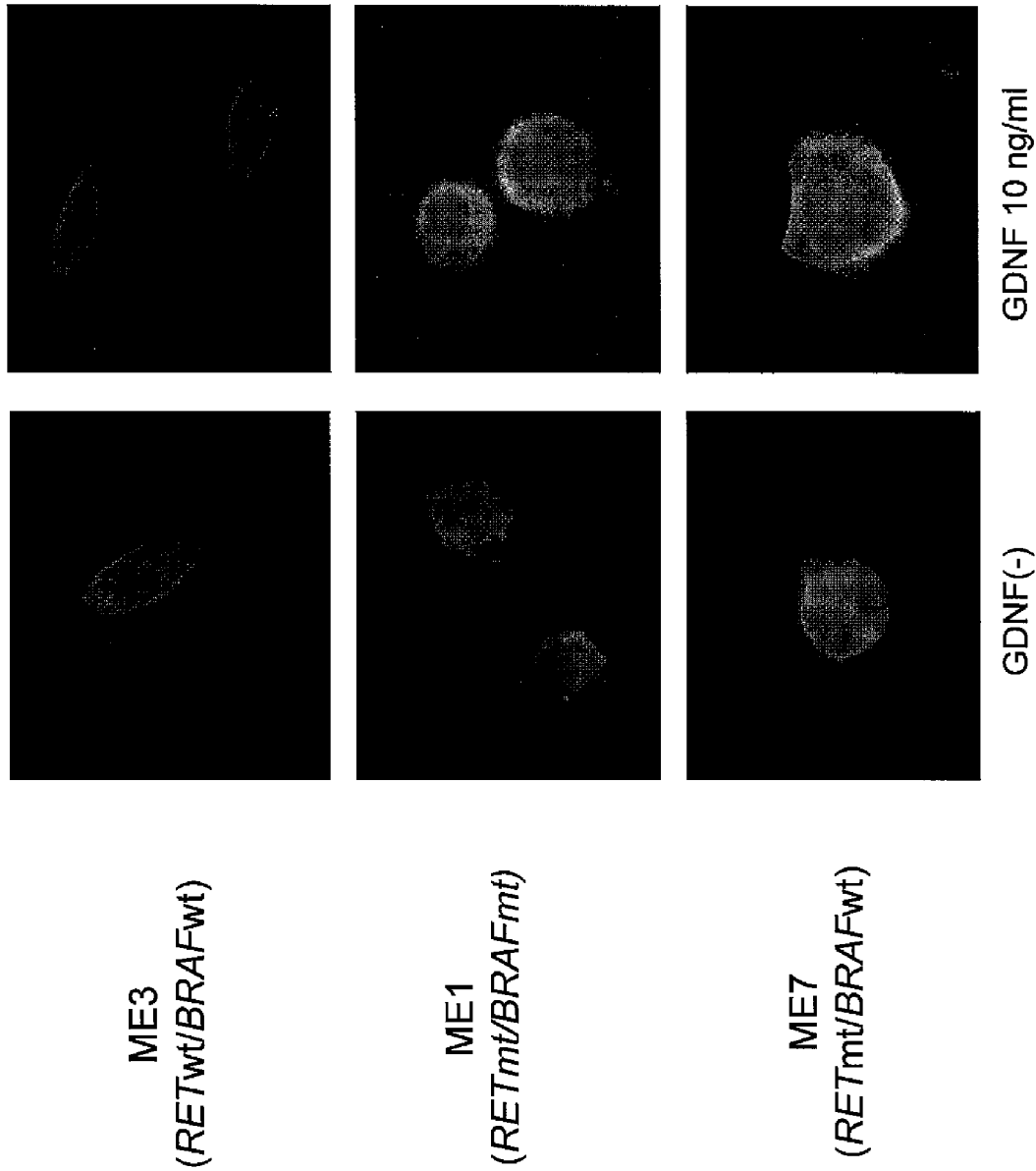
FIG. 7. Actin polymerization by GDNF. Upper panels show no actin polymerization induced 48 hrs after 10 ng/ml of GDNF treatment in ME3 (RETwt/BRAFwt). The arrows in middle and lower panels show actin polymerization (filopodia) induced intensely by GDNF in ME1 (RETmt/BRAFmt) and ME7 (RETmt/BRAFwt), respectively.

Morphological alterations occurred during migration of melanoma cells after GDNF treatment. Actin polymerization on the cell surface was observed to confirm cell motility induced by GDNF in RETmt cells. Based on Based on the migration assays, we selected 10 ng/ml of GDNF for assessment of cell motility. Actin polymerization, such as filopodia, necessary for cell migration, was visualized using Alexa Fluor® 568 phalloidin staining. Administration of GDNF induced filopodia in RETmt cell lines (ME1, ME7), but not in the RETwt cell line (ME3) (FIG. 7). These results support the findings of the cell migration and invasion assays; filopodia or lamellipodia represent activation of morphological changes leading to cell motility.

Discussion

RET gene expression has been detected primarily in human tumors of neural crest origin, such as neuroblastoma, pheochromocytoma, and medullary thyroid carcinoma (10). RETmt was originally found in radiation-induced thyroid tumors and sporadic medullary thyroid cancers (30, 31). We identified a high frequency of RETmt in cutaneous melanomas, particularly more frequently in DMs (non-DMs: 31%, DMs: 61%), whereas RETmt has been detected in 15-20% of the normal population (30-33). The frequency of RETmt in noncancerous tissue from RETmt melanoma specimens was much higher in patients with DM than in those with non-DMs (84% vs. 50%, respectively). The results suggest that RETmt status may reflect more frequent hereditary polymorphisms in DM patients and somatic polymorphisms in non-DM patients, respectively. In previous reports, it was demonstrated that the G691S exon 11 RETmt was present in pancreatic and thyroid cancers (18, 31). This observation suggests that the genetic and/or proteomic status of the cells related to RETmt allows specific signaling pathways to be activated through GDNF. Previously, it was also noted that only certain RET-expressing tissues, such as the thyroid gland, had a rearrangement in RET gene that led to physiological changes (12, 15).

Our study is the first report demonstrating GDNF significantly activates RETmt compared to RETwt melanoma cells in promoting proliferation, migration, and invasion. These findings suggest that RETmt melanoma may have more aggressive invasion and proliferating activity when in the vicinity of neural and other tissues releasing GDNF. Peripheral neural tissues secrete GDNF and are invaded by cutaneous melanomas. Brain metastasis is one of the major causes of death for melanoma patients (34); GDNF secreted by glial cells in the brain could significantly contribute to proliferation and migration of RETmt melanoma cells. Although mutation in the juxtamembrane region may mediate cross-talk between RET protein and signaling pathways of other receptors (12, 15), we demonstrated that there does not appear to be cross-talk involved in GDNF-RET signaling. The observation that RETmt is more frequent in DMs and responsive to the neurotrophic factor GDNF in non-DMs suggests that this RTK may play a significant role in cutaneous melanoma progression overall.

RETmt-GDNF enhanced and prolonged the phosphorylation of the ERK and Akt. PD98059, a MEK1 inhibitor, significantly blocked the cell proliferation induced by GDNF, whereas wortmannin, a PI3K inhibitor, suppressed GDNF-enhanced proliferation of RETmt cells to some extent. These results suggested that both pathways of RET-RAS-RAF-ERK and RET-PI3K-Akt (14) can be activated through RETmt-GDNF activation and are compatible with the results of proliferation assays, in which GDNF enhanced cell proliferation in only RETmt cells. The results of migration and invasion assays showed RET-PI3K pathway played a significant role for cell motility induced by GDNF. A recent report has shown that Akt-induced phosphorylation plays an integral role in the vertical growth of melanoma (35). Possibly, cell motility could be induced by GDNF through activation of both pathways of RET-PI3K-RAC and RET-PI3K-Akt. The assessment of the RET-RAS-ERK pathways becomes complicated as it is known that signal transduction through the BRAFmt (V600E), a member of this pathway, is quite frequent in melanomas; signal transduction through NRAS mutation occurs to a much lesser extent (36). Therefore, using BRAFmt in cell lines with RETmt or RETwt, we demonstrated that GDNF stimulation of RETmt cells was not significantly influenced by BRAFmt presence.

The results showed cells with BRAFmt was not influential on GDNF-induced proliferation, migration and invasion of melanoma cells. Although BRAFmt phosphorylates downstream factors such as MEK or ERK without ligand stimulation (19, 37), GDNF induced more intense phosphorylation of ERK 1/2 in RETmt/BRAFmt cells (ME1), as shown by Western blot analyses. This suggests that BRAFmt only partially phosphorylates the ERK pathway and its downstream factors. Consequently, cells bearing BRAFmt may have no effect on ERK phosphorylation after GDNF stimulation, compatible with the result of our proliferation assay in which BRAFmt had no effect on GDNF-induced proliferation of melanoma cells. These data also confirm our previous finding that BRAFmt is less frequent in primary melanomas (20), and suggests that this mutation is also not significant for progression of all types of cutaneous melanomas. Linkage of sun exposure to BRAFmt may not be clear for all cutaneous melanomas since DMs are known to be more frequently found in chronically sun-exposed areas (3). DMs had a significantly lower level (>3 fold) of BRAFmt compared to non-DMs. This finding supports a previous report on BRAFmt in DMs in a small cohort of patients (38).

There are several new RTK inhibitors affecting RET in clinical trials. Sorafenib (BAY 43-9006, serine/threonine kinase RAF1, and BRAF inhibitor) and semaxanib (SU5416, vascular endothelial cell growth factor receptor inhibitor) are RTK inhibitors that can block RET signaling and suppress growth of RETmt thyroid cancers (39, 40). Sorafenib directly suppresses the kinase activity of RET, and promotes lysosomal degradation of RET protein (41). RETmt melanomas may be more selective targets for using these RTK inhibitors. These inhibitors may be used as strategic target to block RETmt melanomas that may be prone to neurotropism. Our findings of melanoma cells with RETmt/wt and BRAFmt/wt in combination suggest that some of the current clinical trials with these inhibitors may be working through the RETmt pathway. To date, the association of BRAFmt in melanoma with response to Sorafenib alone has not been clearly demonstrated.

RETmt could be a key factor for proliferation and invasion of malignant melanoma cells, and its high incidence in DM may explain why this malignancy often exhibits neurotropism. Future sequencing studies of RET gene will examine for other functional mutations in melanoma. In our study, inhibition of RET signaling suppressed all proliferation and invasion in melanomas. This suggests that RETmt could be a new RTK target for treatment of malignant melanomas; regimens based on RTK inhibitors selective for RET may be particularly promising.

REFERENCES

1. Hoon D S, Kuo C T, Wascher R A, Fournier P, Wang H J, and O'Day S J. Molecular detection of metastatic melanoma cells in cerebrospinal fluid in melanoma patients. J Invest Dermatol 2001; 117:375-8.
2. Jaroszewski D E, Pockaj B A, DiCaudo D J, and Bite U. The clinical behavior of desmoplastic melanoma. Am J Surg 2001; 182:590-5.
3. Quinn M J, Crotty K A, Thompson J F, Coates A S, O'Brien C J, and McCarthy W H. Desmoplastic and desmoplastic neurotropic melanoma: experience with 280 patients. Cancer 1998; 83:1128-35.
4. Livestro D P, Muzikansky A, Kaine E M, et al. Biology of desmoplastic melanoma: a case-control comparison with other melanomas. J Clin Oncol 2005; 23:6739-46.
5. Busam K J. Cutaneous desmoplastic melanoma. Adv Anat Pathol 2005; 12:92-102.
6. Takahashi M, Buma Y, Iwamoto T, Inaguma Y, Ikeda H, and Hiai H. Cloning and expression of the ret proto-oncogene encoding a tyrosine kinase with two potential transmembrane domains. Oncogene 1988; 3:571-8.
7. Takahashi M, Buma Y, and Hiai H. Isolation of ret proto-oncogene cDNA with an amino-terminal signal sequence. Oncogene 1989; 4:805-6.
8. Iwamoto T, Taniguchi M, Asai N, Ohkusu K, Nakashima I, and Takahashi M. cDNA cloning of mouse ret proto-oncogene and its sequence similarity to the cadherin superfamily. Oncogene 1993; 8:1087-91.
9. Zbuk K M and Eng C. Cancer phenomics: RET and PTEN as illustrative models. Nat Rev Cancer 2007; 7:35-45.
10. Takahashi M. The GDNF/RET signaling pathway and human diseases. Cytokine Growth Factor Rev 2001; 12:361-73.
11. Lin L F, Doherty D H, Lile J D, Bektesh S, and Collins F. GDNF: a glial cell line-derived neurotrophic factor for midbrain dopaminergic neurons. Science 1993; 260:1130-2.
12. Airaksinen M S and Saarma M. The GDNF family: signalling, biological functions and therapeutic value. Nat Rev Neurosci 2002; 3:383-94.
13. Busam K J, Zhao H, Coit D G, et al. Distinction of desmoplastic melanoma from non-desmoplastic melanoma by gene expression profiling. J Invest Dermatol 2005; 124:412-8.
14. Kodama Y, Asai N, Kawai K, et al. The RET proto-oncogene: a molecular therapeutic target in thyroid cancer. Cancer Sci 2005; 96:143-8.
15. Runeberg-Roos P and Saarma M. Neurotrophic factor receptor RET: structure, cell biology, and inherited diseases. Ann Med 2007:1-9.
16. Kondo T, Ezzat S, and Asa S L. Pathogenetic mechanisms in thyroid follicular-cell neoplasia. Nat Rev Cancer 2006; 6:292-306.
17. Weber F and Eng C. Update on the molecular diagnosis of endocrine tumors: toward omics-based personalized healthcare? J Clin Endocrinol Metab 2008; 93:1097-104.
18. Sawai H, Okada Y, Kazanjian K, et al. The G691S RET polymorphism increases glial cell line-derived neurotrophic factor-induced pancreatic cancer cell invasion by amplifying mitogen-activated protein kinase signaling. Cancer Res 2005; 65:11536-44.
19. Davies H, Bignell G R, Cox C, et al. Mutations of the BRAF gene in human cancer. Nature 2002; 417:949-54.
20. Shinozaki M, Fujimoto A, Morton D L, and Hoon D S. Incidence of BRAF oncogene mutation and clinical relevance for primary cutaneous melanomas. Clin Cancer Res 2004; 10:1753-7.

21. Melillo R M, Castellone M D, Guarino V, et al. The RET/PTC-RAS-BRAF linear signaling cascade mediates the motile and mitogenic phenotype of thyroid cancer cells. J Clin Invest 2005; 115:1068-81.

22. Dhomen N and Marais R. New insight into BRAF mutations in cancer. Curr Opin Genet Dev 2007; 17:31-9.

23. Sumimoto H, Miyagishi M, Miyoshi H, et al. Inhibition of growth and invasive ability of melanoma by inactivation of mutated BRAF with lentivirus-mediated RNA interference. Oncogene 2004; 23:6031-9.

24. Shinozaki M, O'Day S J, Kitago M, et al. Utility of circulating B-RAF DNA mutation in serum for monitoring melanoma patients receiving biochemotherapy. Clin Cancer Res 2007; 13:2068-74.

25. Fujiwara Y, Chi D D, Wang H, et al. Plasma DNA microsatellites as tumor-specific markers and indicators of tumor progression in melanoma patients. Cancer Res 1999; 59:1567-71.

26. Umetani N, Mori T, Koyanagi K, et al. Aberrant hypermethylation of ID4 gene promoter region increases risk of lymph node metastasis in T1 breast cancer. Oncogene 2005; 24:4721-7.

27. Goto Y, Matsuzaki Y, Kurihara S, et al. A new melanoma antigen fatty acid-binding protein 7, involved in proliferation and invasion, is a potential target for immunotherapy and molecular target therapy. Cancer Res 2006; 66:4443-9.

28. Koyanagi K, O'Day S J, Gonzalez R, et al. Serial monitoring of circulating melanoma cells during neoadjuvant biochemotherapy for stage III melanoma: outcome prediction in a multicenter trial. J Clin Oncol 2005; 23:8057-64.

29. Gumireddy K, Sun F, Klein-Szanto A J, et al. In vivo selection for metastasis promoting genes in the mouse. Proc Natl Acad Sci USA 2007; 104:6696-701.

30. Bounacer A, Du Villard J A, Wicker R, et al. Association of RET codon 691 polymorphism in radiation-induced human thyroid tumours with C-cell hyperplasia in peritumoural tissue. Br J Cancer 2002; 86:1929-36.

31. Elisei R, Cosci B, Romei C, et al. RET exon 11 (G691S) polymorphism is significantly more frequent in sporadic medullary thyroid carcinoma than in the general population. J Clin Endocrinol Metab 2004; 89:3579-84.

32. Ceccherini I, Hofstra R M, Luo Y, et al. DNA polymorphisms and conditions for SSCP analysis of the 20 exons of the ret proto-oncogene. Oncogene 1994; 9:3025-9.

33. Stephens L A, Powell N G, Grubb J, et al. Investigation of loss of heterozygosity and SNP frequencies in the RET gene in papillary thyroid carcinoma. Thyroid 2005; 15:100-4.

34. Selek U, Chang E L, Hassenbusch S J, 3rd, et al. Stereotactic radiosurgical treatment in 103 patients for 153 cerebral melanoma metastases. Int J Radiat Oncol Biol Phys 2004; 59:1097-106.

35. Govindarajan B, Sligh J E, Vincent B J, et al. Overexpression of Akt converts radial growth melanoma to vertical growth melanoma. J Clin Invest 2007; 117:719-29.

36. Curtin J A, Busam K, Pinkel D, and Bastian B C. Somatic activation of KIT in distinct subtypes of melanoma. J Clin Oncol 2006; 24:4340-6.

37. Satyamoorthy K, Li G, Gerrero M R, et al. Constitutive mitogen-activated protein kinase activation in melanoma is mediated by both BRAF mutations and autocrine growth factor stimulation. Cancer Res 2003; 63:756-9.

38. Davison J M, Rosenbaum E, Barrett T L, et al. Absence of V599E BRAF mutations in desmoplastic melanomas. Cancer 2005; 103:788-92.

39. Carlomagno F, Anaganti S, Guida T, et al. BAY 43-9006 inhibition of oncogenic RET mutants. J Natl Cancer Inst 2006; 98:326-34.

40. Mologni L, Sala E, Cazzaniga S, et al. Inhibition of RET tyrosine kinase by SU5416. J Mol Endocrinol 2006; 37:199-212.

41. Plaza-Menacho I, Mologni L, Sala E, et al. Sorafenib functions to potently suppress RET tyrosine kinase activity by direct enzymatic inhibition and promoting RET lysosomal degradation independent of proteasomal targeting. J Biol Chem 2007; 282:29230-40.

All publications cited herein are incorporated by reference in their entirety.

What is claimed is:

1. A method of determining or predicting aggressiveness of a melanoma cancer based on the presence or absence of a RET (REarranged during Transfection) mutation in a melanoma cell from a human subject having melanoma cancer or a human melanoma cell culture comprising:

detecting the presence of a RET G691S mutation in the melanoma cell from a human subject having melanoma cancer or a human melanoma cell culture; and determining or predicting that the melanoma cancer is a more aggressive melanoma cancer if the RET G691S mutation is present in the melanoma cell than if the RET G691S mutation is not present in the melanoma cell.

2. The method of claim 1, wherein the melanoma cancer is DM (desmoplastic melanoma), non-DM, metastatic, or primary.

3. The method of claim 1, further comprising detecting a BRAF (V-raf murine sarcoma viral oncogene homolog B1) V600E mutation in the melanoma cell.

4. The method of clam 3, wherein the melanoma is DM, non-DM, metastatic, or primary.

5. The method of claim 1, wherein the detection of a G691S RET mutation is accomplished by Southern blot, polymerase chain reaction (PCR), sequencing, a peptide nucleic acid-locked nucleic acid clamp method, Northern blot, reverse transcriptase-polymerase chain reaction (RT-PCR), immunohistochemistry or Western blot.

6. The method of claim 1, wherein the aggressiveness of the melanoma cancer is determined by enhanced proliferation, more vigorous migration and more vigorous invasion of the melanoma cells when the RET mutation is present as compared to when the RET mutation is not present.

* * * * *

SEQUENCE LISTING

<160> NUMBER OF SEQ ID NOS: 22

<210> SEQ ID NO 1
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1
aactgcagcg aggagatgta                                              20

<210> SEQ ID NO 2
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2
ccgcaaggtc caagtagtct                                              20

<210> SEQ ID NO 3

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 3
ccctccgggt taagaacaag                                                   20

<210> SEQ ID NO 4
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 4
gatttcagct tctgtgcctg t                                                 21

<210> SEQ ID NO 5
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 5
gtgatggcac accagaatga                                                   20

<210> SEQ ID NO 6
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 6
ccataggctc aggagcagaa                                                   20

<210> SEQ ID NO 7
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 7
gggtgtgaac catgagaagt                                                   20

<210> SEQ ID NO 8
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 8
gactgtggtc atgagtcct                                                    19

<210> SEQ ID NO 9
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 9
```

```
tcttctccag gtctttgctg atgtcc                                          26

<210> SEQ ID NO 10
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 10
aaattcccac tcatgttttg ccacc                                           25

<210> SEQ ID NO 11
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 11
ctcttttctc ctgcacgctt ccctt                                           25

<210> SEQ ID NO 12
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 12
cagcaatgcc tcctgcacca ccaa                                            24

<210> SEQ ID NO 13
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 13
ccttcccggt cagctactc                                                  19

<210> SEQ ID NO 14
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 14
accctcacca ggatcttgaa                                                 20

<210> SEQ ID NO 15
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 15
agtgcccgcc ggccct                                                     16

<210> SEQ ID NO 16
<211> LENGTH: 19
<212> TYPE: DNA
<213> ORGANISM: Artificial sequence
<220> FEATURE:
```

```
<223> OTHER INFORMATION: Synthetic oligonucleotide

<400> SEQUENCE: 16
cttccggtgc ccgccggcc                                                  19

<210> SEQ ID NO 17
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 17
cctcacagta aaataggtg                                                  20

<210> SEQ ID NO 18
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 18
atagcctcaa ttcttacca                                                  19

<210> SEQ ID NO 19
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 19
ctacagagaa atctcgat                                                   18

<210> SEQ ID NO 20
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 20
ctacagtgaa atctcg                                                     16

<210> SEQ ID NO 21
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 21
taccacaagt ttgcccacaa                                                 20

<210> SEQ ID NO 22
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 22
gagggcaggg gatcttcc                                                   18
```